United States Patent
Wang et al.

(10) Patent No.: US 9,556,171 B2
(45) Date of Patent: Jan. 31, 2017

(54) CERTAIN PROTEIN KINASE INHIBITORS

(71) Applicant: Shanghai Fochon Pharmaceutical Co., Ltd., Shanghai (CN)

(72) Inventors: Weibo Wang, Moraga, CA (US); Xingdong Zhao, Moraga, CA (US); Quan Yuan, Chongqing (CN); Hailong Shi, Chongqing (CN); Qiang Tian, Chongqing (CN); Qihong Liu, Chongqing (CN); Zuwen Zhou, Chongqing (CN); Xianlong Wang, Chongqing (CN); Zhifang Chen, Chongqing (CN); Ling Chen, Chongqing (CN); Haohan Tan, Chongqing (CN); Bo Fang, Chongqing (CN); Lihua Jiang, Chongqing (CN); Yanxin Liu, Chongqing (CN); Jing Sun, Chongqing (CN); Fanxin Zeng, Chongqing (CN); Tongshuang Li, Surrey (CA)

(73) Assignee: Shanghai Fochon Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/785,205

(22) PCT Filed: Apr. 18, 2014

(86) PCT No.: PCT/CN2014/075664
§ 371 (c)(1),
(2) Date: Oct. 16, 2015

(87) PCT Pub. No.: WO2014/169843
PCT Pub. Date: Oct. 23, 2014

(65) Prior Publication Data
US 2016/0083376 A1   Mar. 24, 2016

Related U.S. Application Data

(60) Provisional application No. 61/813,190, filed on Apr. 18, 2013.

(51) Int. Cl.
*A01N 43/58* (2006.01)
*A01N 43/60* (2006.01)
*A61K 31/50* (2006.01)
*A61K 31/495* (2006.01)
*C07D 471/04* (2006.01)
*A61K 31/5025* (2006.01)
*C07D 487/04* (2006.01)

(52) U.S. Cl.
CPC ......... *C07D 471/04* (2013.01); *A61K 31/5025* (2013.01); *C07D 487/04* (2013.01)

(58) Field of Classification Search
None
See application file for complete search history.

(56) References Cited

U.S. PATENT DOCUMENTS

2005/0256123 A1   11/2005   Marlow et al.

FOREIGN PATENT DOCUMENTS

WO   WO2005/051301   *   6/2005

OTHER PUBLICATIONS

Kandeel, et. al., Heterocycles (1986), 24(9), 2455-61.*
International Preliminary Report on Patentability (Chapter I of the Patent Cooperation Treaty) and Written Opinion of the International Searching Authority corresponding to International Patent Application No. PCT/CN2014/075664 dated Oct. 20, 2015.
International Search Report corresponding to PCT/CN2014/075664 mailed on Jul. 16, 2014.
Ji et al., "ERK MAP Kinase Activation in Superficial Spinal Cord Neurons Induces Prodynorphin and NK-1 Upregulation and Contributes to Persistent Inflammatory Pain Hypersensitivity," J. Neurosci., 22:478-485 (2002).
Pearson, G. et al., "Mitogen-Activated Protein (MAP) Kinase Pathways: Regulation and Physiological Functions," Endocr. Rev., 22(2):153-183 (2001).
Wang et al., "Significant Neuroprotection against Ischemic Brain Injury by Inhibition of the MEK1 Protein Kinase in Mice: Exploration of Potential Mechanism Associated with Apoptosis," J. Pharmacal. Exp. Ther., 304: 172-178 (2003).

* cited by examiner

*Primary Examiner* — Jeffrey H Murray
(74) *Attorney, Agent, or Firm* — Jenkins, Wilson, Taylor & Hunt, PA

(57) ABSTRACT

Disclosed herein are protein kinase inhibitors, more particularly pyridazine derivatives and pharmaceutical compositions thereof, and method of use thereof.

15 Claims, No Drawings

CERTAIN PROTEIN KINASE INHIBITORS

Provided are certain compounds and/or pharmaceutically acceptable salts thereof which can inhibit kinase activity of MEK and may be useful for the treatment of hyper-proliferative diseases like cancer and inflammation.

Hyperproliferative diseases like cancer and inflammation are attracting the scientific community to provide therapeutic benefits. In this regard efforts have been made to identify and target specific mechanisms which play a role in proliferating the diseases.

Mitogen-activated protein (MAP) kinase is relevant to many cancers. MAP kinases specifically phosphorylate serine/threonine residues of proteins, that are activated by a variety of external stimuli (for example, mitogens and growth factors) to manifest its actions inside the cell. The activation of MAP kinases regulates many functions of the cells with physiological implications such as cell growth, survival, apoptosis, differentiation, proliferation and gene expression (Pearson, G. et al., *Endocr. Rev.*, 2001, 153-183).

MAP kinase pathway can be activated when a growth factor binds to its receptor tyrosine kinase. This interaction promotes RAS association with RAF and initiates a phosphorylation cascade through MEKs to ERKs. The phosphorylated-ERK upon its translocation to nucleus activates several transcription factors to induce the expression of many genes required for cell survival and proliferation (Sebolt, J. S.; Herrera, R. *Nature Rev. Can.* 2004, 937-947).

Mitogen-activated protein/extracellular signal-regulated kinase kinase (MEK) is an attractive therapeutic target because the only known substrates for MEK phosphorylation are the MAP kinases, ERK1 and ERK2. Constitutive activation of MEK/ERK was been found in pancreatic, colon, lung, kidney and ovarian primary tumor samples.

Furthermore, in additional to their potential as anti-tumor agents, MEK inhibitors are described in the art as having potential use for the treatment of anti-inflammatory diseases (*Biochem Biophy. Res. Corn.*, 2000, 268: 647), stroke (*J. Pharmacal. Exp. Ther.* 2003, 304: 172), and Pain (*J. Neurosci.* 2002, 22:478, 2002);

Therefore, the MEK-ERK signal transduction pathway is an attractive pathway to target for therapeutic intervention. Therefore, there is a need for MEK inhibitors that have at least one advantageous property selected from potency, stability, toxicity, pharmacodynamics properties and pharmacokinetics properties as an alternative for the treatment of hyper-proliferative diseases like cancer and inflammation. In this regard, a class of MEK inhibitors is provided herein.

DISCLOSURE OF THE INVENTION

Provided is at least one compound of formula (I):

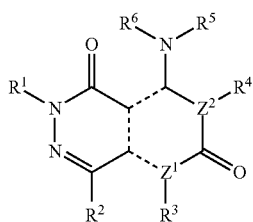
(I)

and/or at least one pharmaceutically acceptable salt thereof, wherein:

$Z^1$ and $Z^2$ are independently selected from C and N;

a

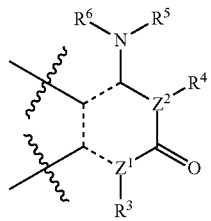

moiety is

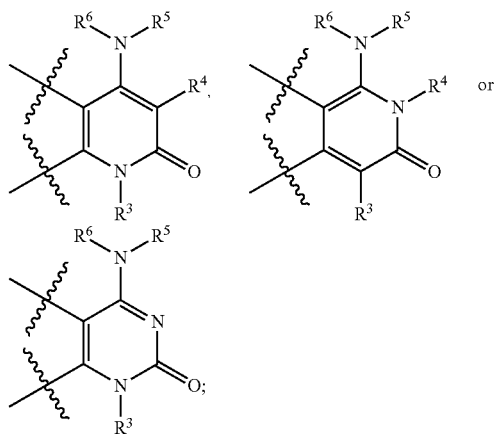

$R^1$, $R^2$ and $R^5$ are independently selected from:
hydrogen,
halogen,
CN,
nitro,
$NH_2$,
$(CH_2)_m$-Q
$C_{1-6}$ alkyl,
$C_{2-6}$ alkenyl,
$C_{2-6}$ alkynyl,
$C_{3-10}$ cycloalkyl, and
wherein $C_{1-6}$ alkyl, $C_{2-6}$ alkenyl, $C_{2-6}$ alkynyl and $C_{3-10}$ cycloalkyl are each unsubstituted or substituted with at least one substituent, such as one, two, three, or four substituents, independently selected from $R^7$;

Q is selected from
aryl,
heteroaryl,
$C_{3-10}$ cycloalkyl, and
heterocyclyl,
wherein aryl, heteroaryl, $C_{3-10}$ cycloalkyl, and heterocyclyl are each unsubstituted or substituted with at least one substituent, such as one, two, three, or four substituents, independently selected from $R^8$;

$R^3$, $R^4$ and $R^6$ are independently selected from:
hydrogen,
halogen,
CN,
nitro,
$C_{1-6}$ alkyl,
$C_{2-6}$ alkenyl, and
$C_{2-6}$ alkynyl, wherein $C_{1-6}$ alkyl, $C_{2-6}$ alkenyl and $C_{2-6}$ alkynyl are each unsubstituted or substituted with at least one substituent, such as one, two, three, or four substituents, independently selected from $R^7$;

each $R^7$ is independently selected from:
halogen,
CN,
nitro,
$C(=O)R^b$,
$C(=O)OR^b$,
$C(=O)NR^aR^a$,
$C(=NR^a)NR^aR^a$,
$OR^a$,
$OC(=O)R^b$,
$OC(=O)NR^aR^a$,
$OC_{1-6}$ alkylN($R^a$)C(=O)$OR^b$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O)OR^b$,
$S(=O)_2N(R^a)C(=O)NR^aR^a$,
$(CR^cR^c)_nNR^aR^a$,
$N(R^a)C(=O)R^b$,
$N(R^a)C(=O)OR^b$,
$N(R^a)C(=O)NR^aR^a$,
$N(R^a)C(NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$,
$(CR^cR^c)_nC_{4-8}$ heterocycloalkyl,
$(CR^cR^c)_n$ aryl,
$(CR^cR^c)_n$heteroaryl,
$(CR^cR^c)_nO(CR^cR^c)_n$ aryl,
$(CR^cR^c)_nC_{3-8}$ cycloalkyl,
$(CR^cR^c)_nC_{4-8}$ heterocycloalkyl,
$(CR^cR^c)_nO(CR^cR^c)CF_3$,
$(CR^cR^c)_n$ N(CR$^c$R$^c$)OR$^a$,
$(CR^cR^c)_nN(R^a)(CR^cR^c)_n$ aryl,
$(CR^cR^c)_nN(R^a)(CR^cR^c)_n$ heteroaryl,
$(CR^cR^c)_nO(CR^cR^c)_n$ heteroaryl,
$C_{1-6}$ alkyl,
$C_{2-6}$ alkenyl, and
$C_{2-6}$ alkynyl, wherein $C_{1-6}$ alkyl, $C_{2-6}$ alkenyl, $C_{2-6}$ alkynyl, aryl, heteroaryl, $C_{3-8}$ cycloalkyl and $C_{4-8}$ heterocycloalkyl are each unsubstituted or substituted with at least one substituent, such as one, two, three, or four substituents, independently selected from:
halogen,
oxo,
$C_{1-6}$ alkyl,
CN,
nitro,
$C(=O)R^b$,
$C(=O)OR^b$,
$C(=O)NR^aR^a$,
$C(NR^a)NR^aR^a$,
$OR^a$,
$OC(=O)R^b$,
$OC(=O)NR^aR^a$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O)OR^b$,
$S(=O)_2N(R^a)C(=O)NR^aR^a$,
$NR^aR^a$,
$N(R^a)C(=O)R^b$,
$N(R^a)C(=O)OR^b$,
$N(R^a)C(=O)NR^aR^a$,
$N(R^a) C(=NR^a)NR^aR^a$,
$N(R^a) S(=O)_2R^b$,
$N(R^a) S(=O)_2NR^aR^a$,
$NR^aC_{2-6}$ alkylNR$^a$R$^a$,
$NR^aC_{2-6}$ alkylOR$^a$,
$N(R^a)(CR^aR^a)_n$—Y,
$(CR^aR^a)_n$—Y,
$(CR^aR^a)_nC_{3-8}$ cycloalkyl, and
$(CR^aR^a)_nOR^a$;

each $R^8$ is independently selected from:
halogen,
oxo,
$OCHF_2$,
$OCF_3$,
CN,
nitro,
$C(=O)R^b$,
$C(=O)OR^b$,
$C(=O)NR^aR^a$,
$C(=NR^a)NR^aR^a$,
$OR^a$,
$OC(=O)R^b$,
$OC(=O)NR^aR^a$,
$OC_{1-6}$ alkylN($R^a$)C(=O)$OR^b$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O)OR^b$,
$S(=O)_2N(R^a)C(=O)NR^aR^a$,
$NR^aR^a$,
$N(R^a)C(=O)R^b$,
$N(R^a)C(=O) OR^b$,
$N(R^a)C(=O)NR^aR^a$,
$N(R^a)C(=NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$,
$C_{1-6}$ alkyl,
$C_{2-6}$ alkenyl, and
$C_{2-6}$ alkynyl, wherein $C_{1-6}$ alkyl, $C_{2-6}$ alkenyl, and $C_{2-6}$ alkynyl are each unsubstituted or substituted with at least one substituent, such as one, two, three, or four substituents, independently selected from:
halogen,
CN,
nitro,
$C(=O)R^b$, C(=O)OR$^b$,
C(=O)NR$^a$R$^a$,
C(=NR$^a$)NR$^a$R$^a$,
OR$^a$,
OC(=O)R$^b$,
OC(=O)NR$^a$R$^a$,
OC(=O)N(R$^a$)S(=O)$_2$R$^b$,
OC$_{2-6}$alkylNR$^a$R$^a$,
OC$_{2-6}$alkylOR$^a$,
SR$^a$,
S(=O)R$^b$,
S(=O)$_2$R$^b$,
S(=O)$_2$NR$^a$R$^a$,
S(=O)$_2$N(R$^a$)C(=O)R$^b$,
S(=O)$_2$N(R$^a$)C(=O)OR$^b$,
S(=O)$_2$N(R$^a$)C(=O)NR$^a$R$^a$,
NR$^a$R$^a$,
N(R$^a$)C(=O)R$^b$,
N(R$^a$)C(=O)OR$^b$,
N(R$^a$)C(=O)NR$^a$R$^a$,
N(R$^a$)C(=NR$^a$)NR$^a$R$^a$,
N(R$^a$)S(=O)$_2$R$^b$,
N(R$^a$)S(=O)$_2$NR$^a$R$^a$,
NR$^a$C$_{2-6}$alkylNR$^a$R$^a$,
NR$^a$C$_{2-6}$alkylOR$^a$,
N(R$^a$)(CR$^a$R$^a$)$_n$—Y,
(CR$^a$R$^a$)$_n$—Y, and
(CR$^a$R$^a$)$_n$OR$^a$;

each R$^a$ is independently selected from hydrogen and R$^b$;
each R$^b$ is independently selected from:
C$_{1-6}$ alkyl,
C$_{2-6}$ alkenyl,
C$_{2-6}$ alkynyl,
aryl,
heteroaryl,
C$_{3-8}$ cycloalkyl, and
C$_{4-8}$ heterocycloalkyl,
wherein the C$_{1-6}$ alkyl, C$_{2-6}$ alkenyl, C$_{2-6}$ alkynyl, aryl, heteroaryl, C$_{3-8}$ cycloalkyl and C$_{4-8}$ heterocycloalkyl are each unsubstituted or substituted with at least one substituent, such as one, two, three, or four substituents, independently selected from:
halogen,
CN,
OH,
S(=O)$_2$R$^b$,
OC$_{2-6}$alkylOR$^a$,
C$_{1-4}$ alkyl,
C$_{1-3}$ haloalkyl,
OC$_{1-4}$ alkyl,
NH$_2$, and
NR$^a$R$^a$;

or R$^a$ and R$^b$ together with the carbon atoms and/or heteroatoms to which they are attached can form a 4-10 membered ring containing 0, 1, 2 or 3 heteroatoms independently selected from sulfur and nitrogen;
each R$^c$ is independently selected from:
hydrogen,
OR$^a$,
NR$^a$R$^a$,
C$_{1-6}$ alkyl, and
CR$^c$R$^c$ can form a C$_{3-8}$ cycloalkyl ring;
Y is selected from:
aryl,
heteroaryl,
C$_{3-10}$ cycloalkyl, and
heterocyclyl, wherein aryl, heteroaryl, C$_{3-10}$ cycloalkyl, and heterocyclyl are each unsubstituted or substituted with at least one substituent, such as one, two, three, or four substituents, independently selected from:
C$_{1-8}$ alkyl,
C$_{2-6}$ alkenyl,
C$_{2-6}$ alkynyl,
C$_{1-4}$ haloalkyl,
halogen,
CN,
nitro,
C(=O)R$^b$,
C(=O)OR$^b$,
C(=O)NR$^a$R$^a$,
C(NR$^a$)NR$^a$R$^a$,
OR$^a$,
OC(=O)R$^b$,
OC(=O)NR$^a$R$^a$,
OC(=O)N(R$^a$)S(=O)$_2$R$^b$,
OC$_{2-6}$alkylNR$^a$R$^a$,
OC$_{2-6}$alkylOR$^a$,
SR$^a$,
S(=O)R$^b$,
S(=O)$_2$R$^b$,
S(=O)$_2$NR$^a$R$^a$,
S(=O)$_2$N(R$^a$)C(=O)R$^b$,
S(=O)$_2$N(R$^a$)C(=O) OR$^b$,
S(=O)$_2$N(R$^a$)C(=O)NR$^a$R$^a$,
NR$^a$R$^a$,
N(R$^a$)C(=O)R$^b$,
N(R$_a$) C(=O) OR$^b$,
N(R$^a$)C(=O)NR$^a$R$^a$,
N(R$^a$)C(=NR$^a$)NR$^a$R$^a$,
N(R$^a$)S(=O)$_2$R$^b$,
N(R$^a$)S(=O)$_2$NR$^a$R$^a$,
NR$^a$C$_{2-6}$alkylNR$^a$R$^a$, and
NR$^a$C$_{2-6}$alkylOR$^a$;
each m is selected from 0, 1, 2, 3, and 4,
each n is independently selected from 0, 1, 2, and 3.

In yet another aspect, provided is a pharmaceutical composition comprising at least one compound of formula (I) and/or at least one pharmaceutically acceptable salt thereof and a pharmaceutically acceptable excipient.

In yet another aspect, provided is a method for modulating MEK, comprising administering to a system or a subject in need thereof, a therapeutically effective amount of at least one compound of formula (I) and/or at least one pharmaceutically acceptable salt thereof or pharmaceutical compositions thereof, thereby modulating said MEK.

In yet another aspect, provided is a method to treat, ameliorate or prevent a condition which responds to inhibition of MEK comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition.

Alternatively, provided is a use of at least one compound of formula (I) and/or at least one pharmaceutically acceptable salt thereof in the manufacture of a medicament for treating a condition mediated by MEK. In particular embodiments, the compounds of the disclosure may be used alone or in combination with a second therapeutic agent to treat a condition mediated by MEK, wherein said condition is an autoimmune disease, a transplantation disease, an infectious disease or a cell proliferative disorder.

Furthermore, provided is a method for treating a cell proliferative disorder, comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition.

Alternatively, provided is a use of at least one compound of formula (I) and/or at least one pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

In the above method(s) for using the compounds of the disclosure, at least one compound of formula (I) and/or at least one pharmaceutically acceptable salt thereof may be administered to a system comprising cells or tissues, or to a mammalian subject such as a human or animal subject.

As used herein the following definitions are applicable.

The term "alkyl" refers to both branched and straight-chain saturated aliphatic hydrocarbon groups having the specified number of carbon atoms. Unless otherwise specified, "alkyl" refers to $C_1$-$C_6$ alkyl. For example, $C_1$-$C_6$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "haloalkyl" refers to both branched and straight-chain saturated aliphatic hydrocarbon groups having the specified number of carbon atoms and being substituted with at least one halogen independently selected from fluorine, chlorine, bromine and iodine. Unless otherwise specified, "haloalkyl" refers to $C_1$-$C_6$ haloalkyl. For example, $C_1$-$C_4$, as in "$C_{1-4}$ haloalkyl" is defined to include groups having 1, 2, 3, or 4 carbons in a linear or branched arrangement and being substituted with at least one halogen independently selected from fluorine, chlorine, bromine and iodine.

The term "cycloalkyl" means a saturated aliphatic cyclic hydrocarbon group having the specified number of carbon atoms. Unless otherwise specified, "cycloalkyl" refers to $C_{3-10}$ cycloalkyl. For example, "cycloalkyl" includes but is not limited to cyclopropyl, methyl-cyclopropyl, 2,2-dimethyl-cyclobutyl, 2-ethyl-cyclopentyl, and cyclohexyl.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "aryl" encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" (or "halo") refers to fluorine, chlorine, bromine and iodine.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle" (and variations thereof such as "heterocyclic", or "heterocyclyl") broadly refers to a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

As used herein, "heterocyclylalkyl" refers to alkyl substituted by heterocyclyl. When used in the phrase "heterocyclyl-$C_{1-6}$ alkyl", the term "$C_{1-6}$" refers to the alkyl portion of the moiety and does not describe the number of atoms in the heterocyclyl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is arylalkyl, the aryl portion may be unsubstituted or substituted with at least one substituent, such as one, two, three, or four substituents, independently selected from $R^8$ and the alkyl portion may also be unsubstituted or substituted with at least one substituent, such as one, two, three, or four substituents, independently selected from $R^7$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH2CH2SO2Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "administration of" and or "administering" at least one compound and/or at least one pharmaceutically acceptable salt should be understood to mean providing at least one compound and/or at least one pharmaceutically acceptable salt thereof to the individual in recognized need of treatment.

The term "effective amount" means the amount of the at least one compound and/or at least one pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

In one embodiment, disclosed herein is at least one compound of formula (I):

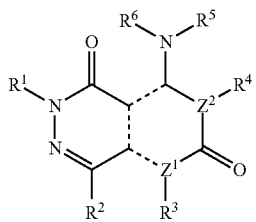

and/or at least one pharmaceutically acceptable salt thereof, wherein:
$Z^1$ and $Z^2$ are independently selected from C and N;
a

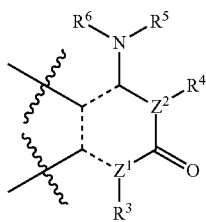

moiety is

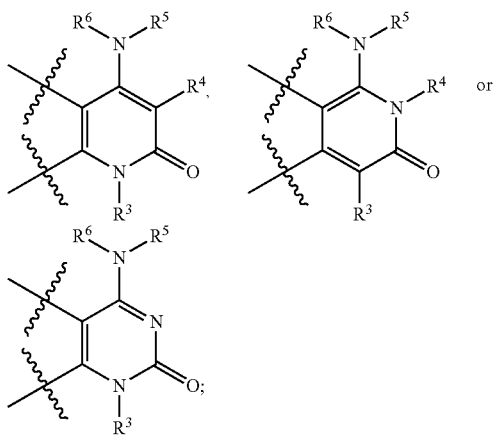

$R^1$, $R^2$, and $R^5$ are independently selected from:
hydrogen,
halogen,
CN,
nitro,
$NH_2$,
$(CH_2)_m$-Q,
$C_{1-6}$ alkyl,
$C_{2-6}$ alkenyl,
$C_{2-6}$ alkynyl,
$C_{3-10}$ cycloalkyl, and
wherein $C_{1-6}$ alkyl, $C_{2-6}$ alkenyl, $C_{2-6}$ alkynyl and $C_{3-10}$ cycloalkyl are each unsubstituted or substituted with at least one substituent, such as one, two, three, or four substituents, independently selected from $R^7$;
Q is selected from
aryl,
heteroaryl,
$C_{3-10}$ cycloalkyl, and
heterocyclyl,
wherein aryl, heteroaryl, C3-10 cycloalkyl, and heterocyclyl are each unsubstituted or substituted with at least one substituent, such as one, two, three, or four substituents, independently selected from R8;
$R^3$, $R^4$, and $R^6$ are independently selected from:
hydrogen,
halogen,
CN,
nitro,
$C_{1-6}$ alkyl,
$C_{2-6}$ alkenyl, and
$C_{2-6}$ alkynyl,
wherein $C_{1-6}$ alkyl, $C_{2-6}$ alkenyl and $C_{2-6}$ alkynyl are each unsubstituted or substituted with at least one substituent, such as one, two, three, or four substituents, independently selected from $R^7$;
each $R^7$ is independently selected from:
halogen,
CN,
nitro,
$C(=O)R^b$,
$C(=O)OR^b$,
$C(=O)NR^aR^a$,
$C(=NR^a)NR^aR^a$,
$OR^a$,
$OC(=O)R^b$,
$OC(=O)NR^aR^a$,
$OC_{1-6}$ alkylN($R^a$)C(=O)$OR^b$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O)$ $OR^b$,
$S(=O)_2N(R^a)C(=O)NR^aR^a$,
$(CR^cR^c)_nNR^aR^a$,
$N(R^a)C(=O)R^b$,
$N(R^a)$ C(=O) $OR^b$,
$N(R^a)C(=O)NR^aR^a$,
$N(R^a)C(NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$, $(CR^cR^c)_nC_{4-8}$ heterocycloalkyl,
$(CR^cR^c)_n$aryl,
$(CR^cR^c)_n$heteroaryl,
$(CR^cR^c)_nO(CR^cR^c)_n$aryl,
$(CR^cR^c)_nC_{3-8}$ cycloalkyl,
$(CR^cR^c)_nC_{4-8}$ heterocycloalkyl,
$(CR^cR^c)_nO(CR^cR^c)_nCF_3$,
$(CR^cR^c)_nN(CR^cR^c)_nOR^a$,
$(CR^cR^c)_nN(R^a)(CR^cR^c)_n$aryl,
$(CR^cR^c)_nN(R^a)(CR^cR^c)_n$heteroaryl,
$(CR^cR^c)_nO(CR^cR^c)_n$heteroaryl,
$C_{1-6}$ alkyl,
$C_{2-6}$ alkenyl, and
$C_{2-6}$ alkynyl,
wherein $C_{1-6}$ alkyl, $C_{2-6}$ alkenyl, $C_{2-6}$ alkynyl, aryl, heteroaryl, $C_{3-8}$ cycloalkyl and $C_{4-8}$ heterocycloalkyl are each unsubstituted or substituted with at least one substituent, such as one, two, three, or four substituents, independently selected from:
halogen,
oxo,
$C_{1-6}$ alkyl,
CN,
nitro,
$C(=O)R^b$,
$C(=O)OR^b$,
$C(=O)NR^aR^a$,
$C(NR^a)NR^aR^a$,
$OR^a$,
$OC(=O)R^b$,
$OC(=O)NR^aR^a$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O) OR^b$,
$S(=O)_2N(R^a)C(=O)NR^aR^a$,
$NR^aR^a$,
$N(R^a)C(=O)R^b$,
$N(R^a)C(=O)OR^b$,
$N(R^a)C(=O)NR^aR^a$,
$N(R^a)C(=NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$,
$N(R^a)(CR^aR^a)_n$—Y,
$(CR^aR^a)_n$—Y,
$(CR^aR^a)_nC_{3-8}$ cycloalkyl, and
$(CR^aR^a)_nOR^a$;
each $R^8$ is independently selected from:
halogen,
oxo,
$OCHF_2$,
$OCF_3$,
CN,
nitro,
$C(=O)R^b$,
$C(=O)OR^b$,
$C(=O)NR^aR^a$,
$C(=NR^a)NR^aR^a$,
$OR^a$,
$OC(=O)R^b$,
$OC(=O)NR^aR^a$,
$OC_{1-6}$ alkylN(R$^a$)C(=O)OR$^b$,
$OC(=O)N(R^a)S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a)C(=O)R^b$,
$S(=O)_2N(R^a)C(=O)OR^b$,
$S(=O)_2N(R^a)C(=O)NR^aR^a$,
$NR^aR^a$,
$N(R^a)C(=O)R^b$,
$N(R^a) C(=O) OR^b$,
$N(R^a)C(=O)NR^aR^a$,
$N(R^a)C(=NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$,
$C_{1-6}$ alkyl,
$C_{2-6}$ alkenyl, and
$C_{2-6}$ alkynyl,
wherein $C_{1-6}$ alkyl, $C_{2-6}$ alkenyl, and $C_{2-6}$ alkynyl are each unsubstituted or substituted with at least one substituent, such as one, two, three, or four substituents, independently selected from:
halogen,
CN,
nitro,
$C(=O)R^b$,
$C(=O)OR^b$,
$C(=O)NR^aR^a$,
$C(NR^a)NR^aR^a$,
$OR^a$,
$OC(=O)R^b$,
$OC(=O)NR^aR^a$,
$OC(=O)N(R^a) S(=O)_2R^b$,
$OC_{2-6}$ alkylNR$^a$R$^a$,
$OC_{2-6}$ alkylOR$^a$,
$SR^a$,
$S(=O)R^b$,
$S(=O)_2R^b$,
$S(=O)_2NR^aR^a$,
$S(=O)_2N(R^a) C(=O)R^b$,
$S(=O)_2N(R^a)C(=O) OR^b$,
$S(=O)_2N(R^a) C(=O)NR^aR^a$,
$NR^aR^a$,
$N(R^a)C(=O)R^b$,
$N(R^a) C(=O) OR^b$,
$N(R^a)C(=O)NR^aR^a$,
$N(R^a)C(=NR^a)NR^aR^a$,
$N(R^a)S(=O)_2R^b$,
$N(R^a)S(=O)_2NR^aR^a$,
$NR^aC_{2-6}$ alkylNR$^a$R$^a$,
$NR^aC_{2-6}$ alkylOR$^a$,
$N(R^a)(CR^aR^a)_n$—Y,
$(CR^aR^a)_n$—Y, and
$(CR^aR^a)_nOR^a$;
each $R^a$ is independently selected from hydrogen and $R^b$;
each $R^b$ is independently selected from:
$C_{1-6}$ alkyl,
$C_{2-6}$ alkenyl,
$C_{2-6}$ alkynyl,
aryl,
heteroaryl, C$_{3-8}$ cycloalkyl, and
C$_{4-8}$ heterocycloalkyl,
wherein the C$_{1-6}$ alkyl, C$_{2-6}$ alkenyl, C$_{2-6}$ alkynyl, aryl, heteroaryl, C$_{3-8}$ cycloalkyl and C$_{4-8}$ heterocycloalkyl are each unsubstituted or substituted with at least one substituent, such as one, two, three, or four substituents, independently selected from:
halogen,
CN,
OH,
S(=O)$_2$R$^b$,
OC$_{2-6}$ alkylOR$^a$,
C$_{1-4}$ alkyl,
C$_{1-3}$ haloalkyl,
OC$_{1-4}$ alkyl,
NH$_2$, and
NR$^a$R$^a$;
or R$^a$ and R$^b$ together with the carbon atoms and/or heteroatoms to which they are attached can form a 4-10 membered ring containing 0, 1, 2 or 3 heteroatoms independently selected from sulfur and nitrogen;
each R$^c$ is independently selected from:
hydrogen,
OR$^a$,
NR$^a$R$^a$,
C$_{1-6}$ alkyl, and
CR$^c$R$^c$ can form a C$_{3-8}$ cycloalkyl ring;
Y is selected from:
aryl,
heteroaryl,
C$_{3-10}$ cycloalkyl, and
heterocyclyl,
wherein aryl, heteroaryl, C$_{3-10}$ cycloalkyl, and heterocyclyl are each unsubstituted or substituted with at least one substituent, such as one, two, three, or four substituents, independently selected from:
C$_{1-8}$ alkyl,
C$_{2-6}$ alkenyl,
C$_{2-6}$ alkynyl,
C$_{1-4}$ haloalkyl,
halogen,
CN,
nitro,
C(=O)R$^b$,
C(=O)OR$^b$,
C(=O)NR$^a$R$^a$,
C(NR$^a$)NR$^a$R$^a$,
OR$^a$,
OC(=O)R$^b$,
OC(=O)NR$^a$R$^a$,
OC(=O)N(R$^a$)S(=O)$_2$R$^b$,
OC$_{2-6}$ alkylNR$^a$R$^a$,
OC$_{2-6}$ alkylOR$^a$,
SR$^a$,
S(=O)R$^b$,
S(=O)$_2$R$^b$,
S(=O)$_2$NR$^a$R$^a$,
S(=O)$_2$N(R$^a$)C(=O)R$^b$,
S(=O)$_2$N(R$^a$)C(=O) OR$^b$,
S(=O)$_2$N(R$^a$)C(=O)NR$^a$R$^a$,
NR$^a$R$^a$,
N(R$^a$)C(=O)R$^b$,
N(R$_a$)C(=O)OR$^b$,
N(R$^a$)C(=O)NR$^a$R$^a$,
N(R$^a$)C(=NR$^a$)NR$^a$R$^a$,
N(R$^a$)S(=O)$_2$R$^b$,
N(R$^a$)S(=O)$_2$NR$^a$R$^a$,
NR$^a$C$_{2-6}$ alkylNR$^a$R$^a$, and
NR$^a$C$_{2-6}$ alkylOR$^a$;
each m is selected from 0, 1, 2, 3, and 4,
each n is independently selected from 0, 1, 2, and 3.
In some embodiments,

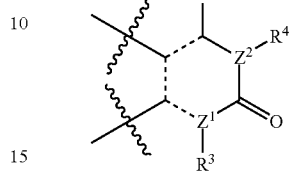

a moiety is

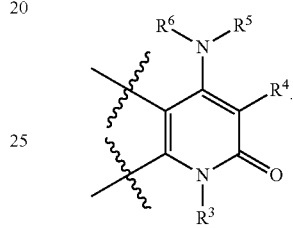

In some embodiments, R$^6$ is hydrogen.
In some embodiments, R$^1$ is selected from hydrogen, C$_{1-6}$ alkyl, C$_{2-6}$ alkenyl and C$_{3-10}$ cycloalkyl, wherein alkyl, alkenyl and cycloalkyl are each unsubstituted or substituted with at least one substituent, such as one, two, three, or four substituents, independently selected from halogen and OR$^a$, wherein R$^a$ is independently selected from hydrogen and C$_{1-6}$ alkyl.
In some embodiments, R$^1$ is methyl, ethyl, propyl, isopropyl, allyl, or cyclopropyl, each is independently unsubstituted or substituted with at least one substituent, such as one, two, three, or four substituents, independently selected from halogen and OR$^a$, wherein R$^a$ is independently selected from hydrogen and C$_{1-6}$ alkyl. In some embodiments, R$^1$ is methyl, ethyl, propyl, isopropyl, allyl, or cyclopropyl, each is independently unsubstituted or substituted with at least one substituent, such as one, two, three, or four substituents, independently selected from halogen and OR$^a$, wherein R$^a$ is independently selected from hydrogen and methyl. In some embodiments, R$^1$ is methyl, ethyl, propyl, isopropyl, allyl, cyclopropyl, 2-fluoroethyl, 2,2-difluoroethyl, 2,3-dihydroxypropyl, or 2-methylxoyethyl.
In some embodiments, R$^2$ is selected from hydrogen, halogen, CN, (CH$_2$)$_m$-Q, C$_{1-6}$ alkyl, or C$_{3-8}$ cycloalkyl, wherein alkyl and cycloalkyl are independently unsubstituted or substituted with at least one substituent, such as one, two, three, or four substituents, independently selected from R$^7$, R$^7$ is as described above.
In some embodiments, R$^2$ is selected from (CH$_2$)$_m$-Q, wherein m is 0, and Q is selected from aryl and heteroaryl, wherein aryl and heteroaryl are each unsubstituted or substituted with at least one substituent, such as one, two, three, or four substituents, independently selected from R$^8$, R$^8$ is as described above.
In some embodiments, R$^2$ is selected from (CH$_2$)$_m$-Q, wherein m is 0, and Q is selected from aryl, wherein aryl is unsubstituted or substituted with at least one substituent, such as one, two, three, or four substituents, independently selected from $R^8$, $R^8$ is as described above.

In some embodiments, $R^2$ is selected from $(CH_2)_m$-Q, wherein m is 0, and Q is phenyl, which is unsubstituted or substituted with at least one substituent, such as one, two, three, or four substituents, independently selected from $R^8$, $R^8$ is as described above.

In some embodiments, $R^2$ is selected from $(CH_2)_m$-Q, wherein m is 0, and Q is phenyl which is unsubstituted or substituted with at least one substituent, such as one, two, three, or four substituents, independently selected from $R^8$, wherein $R^8$ is independently selected from $NR^aR^a$, $N(R^a)C(=O)R^b$, $N(R^a)C(=O)OR^b$, $N(R^a)C(=O)NR^aR^a$, $N(R^a)S(=O)_2R^b$, $N(R^a)S(=O)_2NR^aR^a$, $R^a$ and $R^b$ are as described above.

In some embodiments, $R^2$ is selected from $(CH_2)_m$-Q, wherein m is 0, and Q is phenyl which is unsubstituted or substituted with at least one substituent, such as one, two, three, or four substituents, independently selected from $R^8$, wherein $R^8$ is independently selected from $N(R^a)C(=O)R^b$, $N(R^a)S(=O)_2R^b$, $R^a$ and $R^b$ are as described above. In some embodiments, $R^2$ is selected from $(CH_2)_m$-Q, wherein m is 0, and Q is phenyl which is unsubstituted or substituted with at least one substituent, such as one, two, three, or four substituents, independently selected from $R^8$, wherein $R^8$ is independently selected from $N(R^a)C(=O)R^b$, $N(R^a)S(=O)_2R^b$, wherein $R^a$ is hydrogen or methyl, and $R^b$ is independently selected from methyl, ethyl, isopropyl and cyclopropyl.

In some embodiments, $R^2$ is selected from $(CH_2)_m$-Q, wherein m is 0, and Q is phenyl which is unsubstituted or substituted with at least one substituent, such as one, two, three, or four substituents, independently selected from $R^8$, wherein $R^8$ is independently selected from $N(R^a)C(=O)R^b$, $N(R^a)S(=O)_2R^b$, wherein $R^a$ and $R^b$ together with the carbon atoms and/or heteroatoms to which they are attached form a 5-6 membered ring containing 0, 1, 2 or 3 heteroatoms independently selected from sulfur and nitrogen. In some embodiments, Q is phenyl which is unsubstituted or substituted with at least one substituent, such as one, two, three, or four substituents, independently selected from $R^8$, wherein $R^8$ is independently selected from 2-oxopyrrolidin-1-yl and 1,1-dioxidoisothiazolidin-2-yl.

In some embodiments, $R^3$ is $C_{1-6}$ alkyl.
In some embodiments, $R^3$ is methyl.
In some embodiments, $R^4$ is selected from hydrogen, halogen, CN and $C_{1-6}$ alkyl.
In some embodiments, $R^4$ is selected from halogen and methyl.
In some embodiments, $R^4$ is fluorine or chlorine.
In some embodiments, $R^5$ is $(CH_2)_m$-Q, wherein m and Q are as described above.
In some embodiments, $R^5$ is $(CH_2)_m$-Q, wherein m is 0 and Q are as described above.
In some embodiments, $R^5$ is $(CH_2)_m$-Q, wherein m is 0 and Q is aryl which is unsubstituted or substituted with at least one substituent, such as one, two, three, or four substituents, independently selected from $R^8$.
In some embodiments, $R^5$ is $(CH_2)_m$-Q, wherein m is 0 and Q is phenyl which is unsubstituted or substituted with at least one substituent, such as one, two, three, or four substituents, independently selected from halogen.
In some embodiments, $R^5$ is 2-fluoro-4-iodophenyl or 4-bromo-2-fluorophenyl.

Also provided is at least one compound, selected from:
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenypethanesulfonamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)acetamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propionamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenypisobutyramide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanecarboxamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)methanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenypethanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propane-2-sulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-1-methyl-2,5-dioxo-6-propyl-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-(2-methoxyethyl)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-(2-fluoroethyl)-1-methyl-2,5-dioxo-1,2,5,6-tetrahydropyrido[2,3-d]pyridazin-8-yl)phenyl)cyclopropanesulfonamide,
N-(3-(6-(2,2-difluoroethyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)acetamide, N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)methanesulfonamide, N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)cyclopropanesulfonamide, N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide, N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide, N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide, N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenypethanesulfonamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide, N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)acetamide, N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)methanesulfonamide, N-(3-(6-allyl-3-chloro-4-(2-fluoro-4-iodophenylamino)-1-methyl-2,5-dioxo-1,2,5,6-tetrahydropyrido[2,3-d]pyridazin-8-yl)phenyl)acetamide, N-(3-(3-chloro-6-(2,3-dihydroxypropyl)-4-((2-fluoro-4-iodophenyl)amino)-1-methyl-2,5-dioxo-1,2,5,6-tetrahydropyrido[2,3-d]pyridazin-8-yl)phenyl)acetamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)acetamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propionamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenypethanesulfonamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide, N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide, N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylmethanesulfonamide, N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylpropane-2-sulfonamide, N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylcyclopropanesulfonamide, N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylmethanesulfonamide, N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylpropane-2-sulfonamide, N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylcyclopropanesulfonamide, 6-cyclopropyl-3-fluoro-4-((2-fluoro-4-iodophenyl)amino)-1-methyl-8-(3-(2-oxopyrrolidin-1-yl)phenyl)pyrido[2,3-d]pyridazine-2,5(1H,6H)-dione, 3-fluoro-4-((2-fluoro-4-iodophenyl)amino)-1,6-dimethyl-8-(3-(2-oxopyrrolidin-1-yl)phenyl)pyrido[2,3-d]pyridazine-2,5(1H,6H)-dione, 6-cyclopropyl-8-(3-(1,1-dioxidoisothiazolidin-2-yl)phenyl)-3-fluoro-4-((2-fluoro-4-iodophenyl)amino)-1-methylpyrido[2,3-d]pyridazine-2,5(1H,6H)-dione, and 8-(3-(1,1-dioxidoisothiazolidin-2-yl)phenyl)-3-fluoro-4-((2-fluoro-4-iodophenyl)amino)-1,6-dimethylpyrido[2,3-d]pyridazine-2,5(1H,6H)-dione.

It is noted that the compounds of the present invention may be in the form of a pharmaceutically acceptable salt.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting a Mitogen-Activated Protein Kinase comprising contacting the MEK with a compound of any one of the above embodiments and variations.

In yet another of its aspects, there is provided a method of inhibiting a Mitogen-activated protein/extracellular signal-regulated kinase kinase (MEK) comprising causing a compound of any one of the above embodiments and variations to be present in a subject in order to inhibit the MEK in vivo.

In a further of its aspects, there is provided a method of inhibiting Mitogen-activated protein/extracellular signal-regulated kinase kinase (MEK) comprising administering a first compound to a subject that is converted in vivo to a second compound wherein the second compound inhibits the MEK in vivo, the second compound being a compound according to any one of the above embodiments and variations.

In another of its aspects, there is provided a method of treating a disease state for which a Mitogen-activated protein/extracellular signal-regulated kinase kinase (MEK) possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which a Mitogen-activated protein/extracellular signal-regulated kinase kinase (MEK) possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which a Mitogen-activated protein/extracellular signal-regulated kinase kinase (MEK) possesses activity that contributes to the pathology and/or symptomology of the disease state, the method comprising administering a first compound to a subject that is converted in vivo to a second compound wherein the second compound inhibits the MEK in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another variation of each of the above methods, the Mitogen-activated protein/extracellular signal-regulated kinase kinase (MEK) is MEK1. In still another variation of each of the above methods, the Mitogen-activated protein/extracellular signal-regulated kinase kinase (MEK) is MEK2.

In another of its aspects, there is provided a method of inhibiting an Extracellular Regulated Kinase (ERK) comprising contacting the ERK with a compound of any of the above embodiments and variations.

In still another of its aspects, there is provided a method of inhibiting Extracellular Regulated Kinase (ERK) comprising causing a compound of any of the above embodiments and variations to be present in a subject in order to inhibit the ERK in vivo.

In yet another of its aspects, there is provided a method of inhibiting Extracellular Regulated Kinase (ERK) comprising administering a first compound to a subject that is converted in vivo to a second compound wherein the second compound inhibits the ERK in vivo, the second compound being a compound according to any of the above embodiments and variations.

In one variation of the above methods, the Extracellular Regulated Kinase (ERK) is ERK 1. In another variation of the above methods, the Extracellular Regulated Kinase (ERK) is ERK2.

In another of its aspects, there is provided a method of treating a disease state for which a mutation in the Mek gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a Mitogen-activated protein/extracellular signal-regulated kinase kinase (MEK).

In a further of its aspects, the present invention relates to the use of a compound according to any one of the above embodiments and variations in the manufacture of a medicament for treating a disease state for which a Mitogen-activated protein/extracellular signal-regulated kinase kinase (MEK) possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the disclosure may be administered as the sole active ingredient, or together with other drugs useful against neoplastic diseases or useful in immunomodulating regimens. For example, the compounds of the disclosure may be used in accordance with the disclosure in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

EXAMPLES

Various methods may be developed for synthesizing the at least one compound of formula (I) and/or at least one pharmaceutically acceptable salt thereof. Representative methods for synthesizing the at least one compound of formula (I) and/or at least one pharmaceutically acceptable salt thereof are provided in the Examples. It is noted, however, that the at least one compound of formula (I) and/or at least one pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of the at least one compound of formula (I) and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the at least one compound of formula (I) and/or at least one pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, ninhydrin, or p-anisaldehyde solution. Flash column chromatography was performed on silica gel (230-400 mesh, Merck).

Synthetic Schemes

Synthetic methods for preparing the compounds of the present invention are illustrated in the following Schemes and Examples. Starting materials are commercially available or may be made according to procedures known in the art or as illustrated herein.

The compounds of formula I-a in the present invention can be prepared from intermediates such as those of formula II-h, wherein LG is a leaving group such as halogen or OTf that can be substituted with an appropriate amine under the reacting conditions known in the art to give the corresponding compounds of formula I-a.

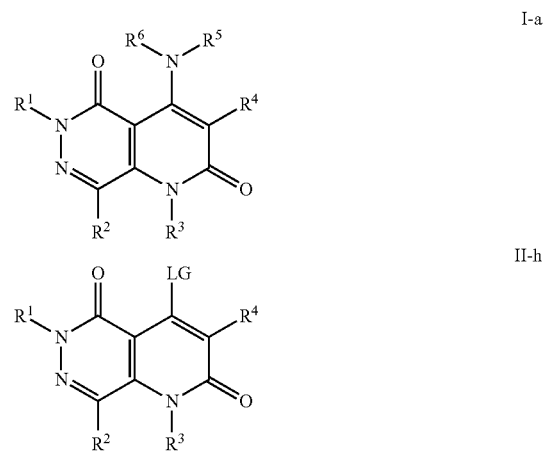

The preparation of these intermediates is described in the following Schemes, wherein X is a halogen such as Cl or F. Compounds of formula IIa may be prepared as illustrated in Scheme 1. Pyridazinone II-b was prepared using method described in Douglas E. Murphy et al., *Tetrahedron Lett.*, 2008, 49, 811. Reaction of pyridazinone II-b with chlorinating agent such as oxalyl chloride followed by the substitution of the resulting chloride with alkyl amine provides amine II-d. Acylation of II-d with a properly substituted ethyl malonyl chloride in a polar solvent such as acetonitrile leads to II-e. Dieckmann condensation of II-e in the presence of a base such as NaOEt gives beta ketone ester II-f. Treatment of II-f with a halogenating agent followed by decarboxylation under such a condition as 2N H$_2$SO$_4$ provides intermediate II-a.

SCHEME 1

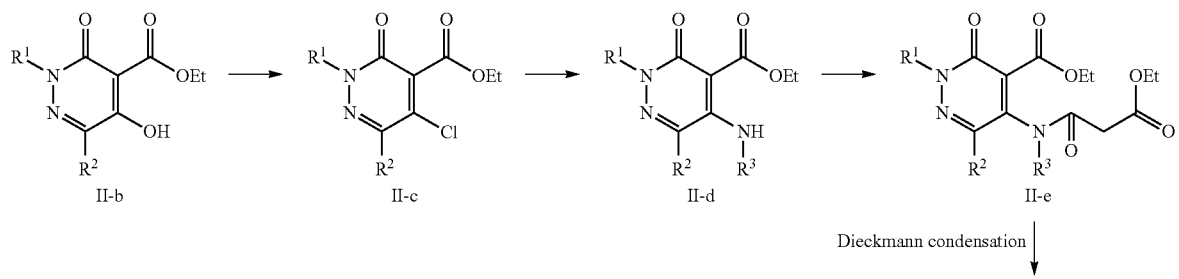

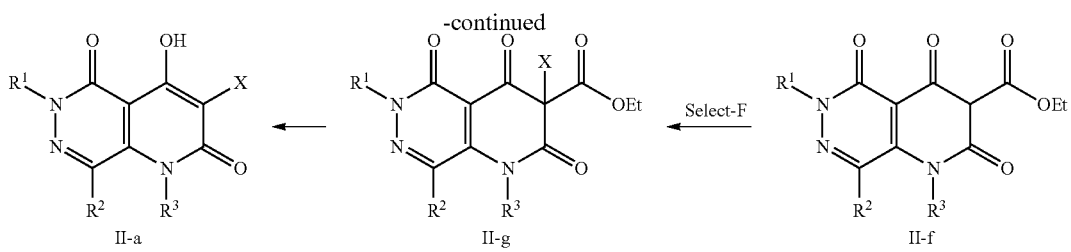
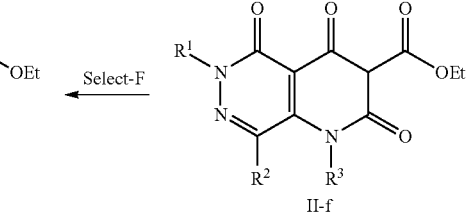

Compounds of formula I-a may be prepared from II-h as illustrated in Scheme 2. Sulfonylation of intermediate II-a with such an agent as sulfonyl anhydride or sulfonyl chloride provide sulfonate ester II-h. Substitution of the resulting sulfonate ester with amine in a solvent such as toluene provides I-a.

Scheme 2

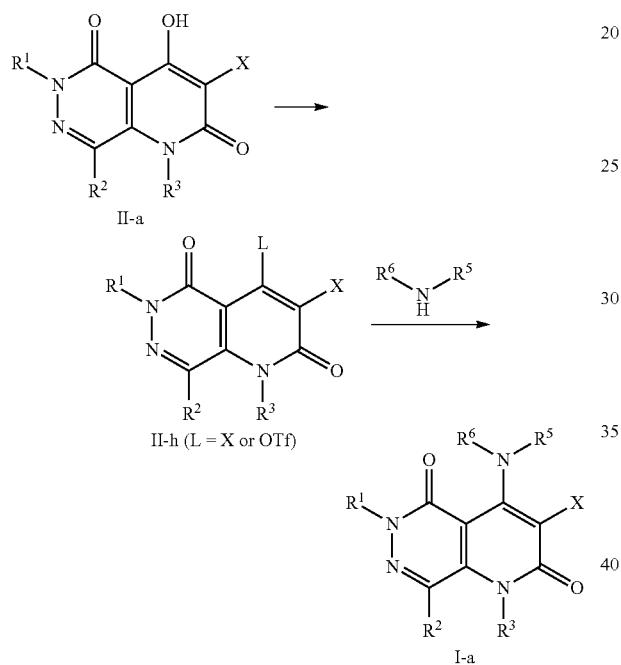

Further modification may be needed depending on the functionalities on the substituents such as $R^2$ and $R^3$.

One such case is illustrated in scheme 3. Reduction of the nitro group in I-aa with a reducing reagent such as $SnCl_2$ provide aniline I-ab, reaction of aniline I-ab with acyl chloride lead to amide I-ac, dihydroxylation of allyl group in I-ac give diol I-ad.

Scheme 3

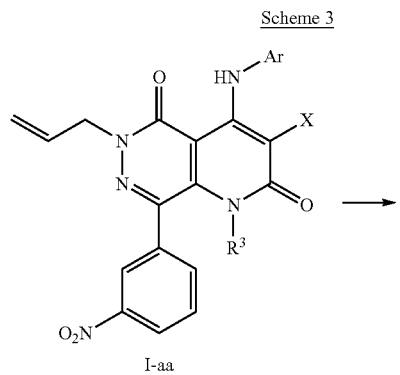

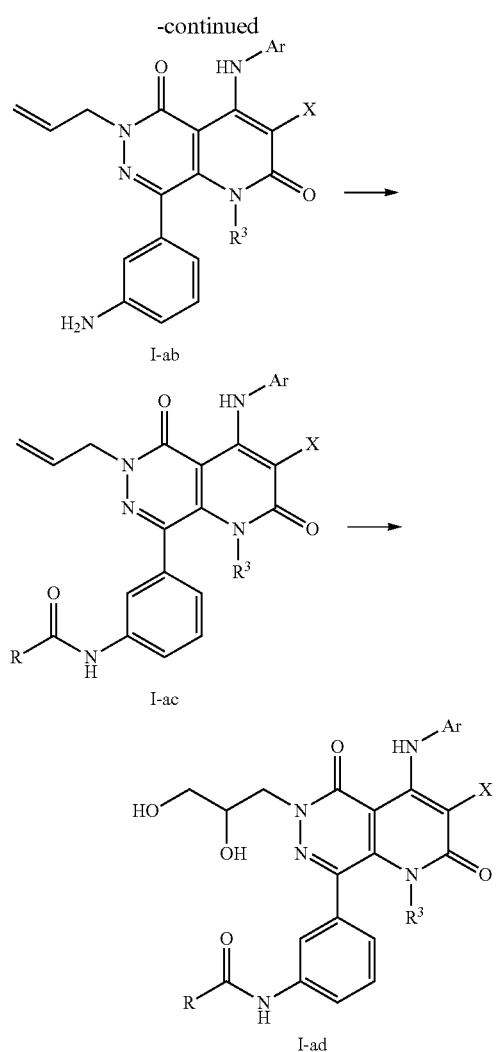

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of the Intermediates

Intermediate A 2-(3-nitrophenyl)-2-oxoacetic acid (A-1)

To a solution of 2-oxo-2-phenylacetic acid (50.0 g, 0.33 mol) in $H_2SO_4$ (400 mL) was added $KNO_3$ (40.4 g, 0.4 mol)

at 0° C. The mixture was warmed to ambient temperature and stirred at 25° C. for 3 h. The reaction mixture was poured into ice-water (1.6 L) and extracted with EtOAc (2×300 mL). The organic extracts were combined and washed with water, brine and dried over anhydrous sodium sulfate and concentrated in vacuo to give the title compound A-1 as crude product (63.1 g, 97%).

Methyl 2-(3-nitrophenyl)-2-oxoacetate (A-2)

To a solution of 2-(3-nitrophenyl)-2-oxoacetic acid (A-1) (60.0 g, 30.8 mmol) in DMF (700 mL) was added $K_2CO_3$ (112 g, 81.2 mmol). After stirring at ambient temperature for 2 h, iodomethane (100 mL, 150.4 mmol) was added dropwise. After being stirred overnight at ambient temperature, the mixture was diluted with EtOAc and washed with water. The organic extracts were washed with brine, dried over anhydrous sodium sulfate, filtered, and concentrated in vacuo. Flash chromatography (PE:ethyl acetate=10:1) of the residue gave the title compound A-2 (44 g, 68%).

Ethyl 3-hydrazinyl-3-oxopropanoate (A-3)

This reagent was prepared according to the method described in literature: E. J. Med. Chem. 2008, 43: 584.

Ethyl 3-(2-(2-ethoxy-1-(3-nitrophenyl)-2-oxoethylidene)hydrazinyl)-3-oxopropanoate (A-4)

To a solution of methyl 2-(3-nitrophenyl)-2-oxoacetate (A-2) (10.0 g, 47.9 mmol) and ethyl 3-hydrazinyl-3-oxopropanoate (A-3) (7.00 g, 47.9 mmol) in EtOH (100 mL) was added $H_2SO_4$ (0.6 mL) at ambient temperature. The mixture was heated at reflux for 2 h. The solution was concentrated and extracted with EtOAc. The organic extracts were washed with water, brine, and dried over anhydrous sodium sulfate. The solid was filtered and the solution was concentrated in vacuo to give the title compound A-4 (14.7 g, E/Z mixture), which was used in the next step without further purification. MS-ESI (m/z): 352 $[M+1]^+$.

Ethyl 5-hydroxy-6-(3-nitrophenyl)-3-oxo-2,3-dihydropyridazine-4-carboxylate (A-5)

To a solution of ethyl 3-(2-(2-ethoxy-1-(3-nitrophenyl)-2-oxoethylidene) hydrazinyl)-3-oxopropanoate (A-4) (14.7 g, 43.6 mmol) in DMF (80 mL) was added $K_2CO_3$ (3.60 g, 26.2 mmol). After being stirred at 80° C. for 3 h, the mixture was cooled to ambient temperature and poured into 3 N HCl (300 mL). The precipitated solid was collected by filtration to give the A-5 (13.4 g, two steps 91%). MS-ESI (m/z): 306 $[M+1]^+$.

Ethyl 5-hydroxy-2-methyl-6-(3-nitrophenyl)-3-oxo-2,3-dihydropyridazine-4-carboxylate (A-6)

To a solution of ethyl 5-hydroxy-6-(3-nitrophenyl)-3-oxo-2,3-dihydropyridazine-4-carboxylate (A-5) (8.00 g, 26.1 mmol) in DMF (150 mL) was added NaH (2.10 g, 52.2 mmol). After being stirred at ambient temperature for 30 min, the solution was cooled to −10° C., iodomethane (1.70 mL, 27.4 mmol) was added dropwise over 10 min. The reaction temperature was slowly warmed up to 10° C. After being stirred at the same temperature for 1 h, the mixture was acidified with 1 N HCl (20 mL) and extracted with EtOAc (300 mL). The organic extracts were washed with water and brine, dried over anhydrous sodium sulfate, and then concentrated in vacuo to give A-6 (8.80 g, 99%) as yellow solid. MS-ESI (m/z): 320 $[M+1]^+$.

Ethyl 5-chloro-2-methyl-6-(3-nitrophenyl)-3-oxo-2,3-dihydropyridazine-4-carboxylate (A-7)

To a solution of ethyl 5-hydroxy-2-methyl-6-(3-nitrophenyl)-3-oxo-2,3-dihydropyridazine-4-carboxylate (A-6) (8.80 g, 27.5 mmol) in DCM (150 mL) was added oxalyl chloride (23.6 mL, 27.5 mmol) and DMF (10 µL). The mixture was stirred at 30-40° C. for 4 h. The solution was concentrated in vacuo to give the title compound A-7 (9.50 g, 100%), MS-ESI (m/z): 338 $[M+1]^+$.

Ethyl 2-methyl-5-(Methylamino)-6-(3-nitrophenyl)-3-oxo-2,3-dihydropyridazine-4-carboxylate (A-8)

To a solution of ethyl 5-chloro-2-methyl-6-(3-nitrophenyl)-3-oxo-2,3-dihydropyridazine-4-carboxylate (A-7) (9.50 g, 27.5 mmol) in DCM (100 mL) at 0° C. was added 50 mL of $MeNH_2$/EtOH (25-30%) dropwise. After being stirred at 0° C. to ambient temperature for 1 h, the mixture was concentrated and extracted with EtOAc (200 mL). The organic extracts were washed with water and brine, dried over anhydrous sodium sulfate, and then concentrated in vacuo to give the title compound A-8 (9.20 g), which was used in next step without further purification. MS-ESI (m/z): 333 $[M+1]^+$.

Ethyl 5-(3-ethoxy-N-methyl-3-oxopropanamido)-2-methyl-6-(3-nitrophenyl)-3-oxo-2,3-dihydropyridazine-4-carboxylate (A-9)

To a solution of ethyl 2-methyl-5-(methylamino)-6-(3-nitrophenyl)-3-oxo-2,3-dihydropyridazine-4-carboxylate (A-8) (9.0 g, 27 mmol) in $CH_3CN$ (120 mL) was added ethyl 3-chloro-3-oxopropanoate (11 mL). Then the mixture was heated to 80° C. for 2 h. The mixture was concentrated in vacuo. Flash chromatography (PE:ethyl acetate=4:1, then DCM:MeOH=10:1) of the residue gave the title compound A-9 (9.4 g). MS-ESI (m/z): 447 $[M+1]^+$.

Ethyl 1,6-dimethyl-8-(3-nitrophenyl)-2,4,5-trioxo-1,2,3,4,5,6-hexahydropyrido[3,2-d]pyridazine-3-carboxylate (A-10)

To a solution of ethyl 5-(3-ethoxy-N-methyl-3-oxopropanamido)-2-methyl-6-(3-nitrophenyl)-3-oxo-2,3-dihydropyridazine-4-carboxylate (A-9) (9.4 g, 21 mmol) in MeOH (100 mL) was added MeONa (2.3 g, 43 mmol) at 0° C. and the mixture was stirred at the same temperature for 1 h. The mixture was concentrated in vacuo, the residue was acidified with 1 N HCl to pH 4-5 and extracted with EtOAc (300 mL). The organic extracts were washed with water and brine, dried over anhydrous sodium sulfate, and then concentrated in vacuo to give the title compound A-10 (6.9 g, 82%). MS-ESI (m/z): 401$[M+1]^+$.

Ethyl 3-fluoro-1,6-dimethyl-8-(3-nitrophenyl)-2,4,5-trioxo-1,2,3,4,5,6-hexahydropyrido[3,2-d]pyridazine-3-carboxylate (A-11)

To a solution of ethyl 1,6-dimethyl-8-(3-nitrophenyl)-2,4,5-trioxo-1,2,3,4,5,6-hexahydropyrido[3,2-d]pyridazine-3-carboxylate (A-10) (4.0 g, 10 mmol) and sodium acetate (1.64 g, 20 mmol) in anhydrous $CH_3CN$ (350 mL) was added Select-Fluor (3.72 g, 10.5 mmol) at 0° C. After being stirred at 0° C. for 3 h, the mixture was concentrated in vacuo. The residue was purified by chromatography on silica gel, eluting with 25% DCM in PE and then with 25% THF in DCM to give the title compound A-11 (4.18 g). MS-ESI (m/z): 419 [M+1]$^+$.

3-Fluoro-4-hydroxy-1,6-dimethyl-8-(3-nitrophenyl) pyrido[2,3-d]pyridazine-2,5(1H,6H)-dione (Intermediate A)

To a solution of crude ethyl 3-fluoro-1,6-dimethyl-8-(3-nitrophenyl)-2,4,5-trioxo-1,2,3,4,5,6-hexahydropyrido[3,2-d]pyridazine-3-carboxylate A-11 (5.3 g) in THF (200 mL) was added 2 N $H_2SO_4$ (200 mL) at room temperature. After being stirred at 90° C. for 5 h, the solution was cooled to room temperature, concentrated in vacuo, and extracted with DCM. The organic extracts were washed with water and brine, dried over anhydrous sodium sulfate, and then concentrated in vacuo to give the title compound Intermediate A (4.7 g). MS-ESI (m/z): 347.0 [M+1]$^+$.

Intermediates B-H listed in Table 1 were prepared following essentially the same procedures as described for the intermediate A by substituting methyl iodide with corresponding alkyl halide listed in the table.

TABLE 1

| RX | Intermediate | Data |
|---|---|---|
| ethyl bromide | B | MS-ESI (m/z): 361.0 [M + 1]$^+$ |
| n-propyl bromide | C | MS-ESI (m/z): 375.0 [M + 1]$^+$ |
| allyl bromide | D | MS-ESI (m/z): 373.0 [M + 1]$^+$ |
| isopropyl bromide | E | MS-ESI (m/z): 375.0 [M + 1]$^+$ |
| 3-fluoropropyl bromide | F | MS-ESI (m/z): 379.0 [M + 1]$^+$ |
| 2,2-difluoropropyl bromide | G | MS-ESI (m/z): 397.0 [M + 1]$^+$ |
| 2-methoxyethyl bromide | H | MS-ESI (m/z): 391.0 [M + 1]$^+$ |

Intermediate I

Ethyl 5-chloro-6-(3-nitrophenyl)-3-oxo-2,3-dihydropyridazine-4-carboxylate (I-1)

To a solution of ethyl 5-hydroxy-6-(3-nitrophenyl)-3-oxo-2,3-dihydropyridazine-4-carboxylate (A-5) (9.40 g, 30.7 mmol) in DCM (60 mL) was added oxalyl chloride (26 mL, 307.2 mmol) at ambient temperature, followed by addition of 3 drops of DMF. After being stirred at 35° C. for 3 h, the reaction mixture was concentrated in vacuo. The residue was dissolved in DCM, washed with water and brine, dried over anhydrous sodium sulfate, and then concentrated in vacuo to give I-1 (9.1 g), which was used in the next step without further purification. MS-ESI (m/z): 324.0 [M+1]$^+$.

Ethyl 5-chloro-2-cyclopropyl-6-(3-nitrophenyl)-3-oxo-2,3-dihydropyridazine-4-carboxylate (I-2)

To a suspension of ethyl 5-chloro-6-(3-nitrophenyl)-3-oxo-2,3-dihydropyridazine-4-carboxylate (I-1) (9.10 g, 28.1 mmol), cyclopropyl boronic acid (4.83 g, 56.2 mmol), 2,2'-bipyridine (5.26 g, 70.2 mmol), sodium carbonate (7.44 g, 33.7 mmol) in anhydrous 1,2-dichloroethane (100 mL) was added diacetoxycopper (6.74 g, 33.7 mmol) under $N_2$ atmosphere at ambient temperature. After being stirred at 70° C. for 2 days, the mixture was diluted with DCM and washed with water and brine. The organic extracts were washed with brine, dried over anhydrous sodiumsulfate, and then concentrated in vacuo. Flash chromatography (silica, hexane:ethyl acetate=3:1) of the residue gave the title compound I-2, (1.94 g). MS-ESI (m/z): 364.0 [M+1]$^+$.

Ethyl 2-cyclopropyl-5-(Methylamino)-6-(3-nitrophenyl)-3-oxo-2,3-dihydropyridazine-4-carboxylate (I-3)

To a solution of ethyl 5-chloro-2-cyclopropyl-6-(3-nitrophenyl)-3-oxo-2,3-dihydropyridazine-4-carboxylate (I-2) (1.9 g) in DCM (18 mL) was added a solution of $MeNH_2$ (10 mL, 27-32%) at 0° C. After being stirred at ambient temperature for 1.5 h, the reaction mixture was concentrated. The residue was dissolved in DCM, washed with water and brine, dried over $Na_2SO_4$ and concentrated to give the crude title compound I-3 (1.53 g), which was used in the next step without further purification. MS-ESI (m/z): 359.0 [M+1]$^+$.

6-Cyclopropyl-3-fluoro-4-hydroxy-1-methyl-8-(3-nitrophenyl)pyrido[2,3-d]pyridazine-2,5(1H,6H)-dione (Intermediate I)

Intermediate I was prepared following the same procedure as described for intermediate A by substituting A-8 with I-3.

Intermediate J

Ethyl 2-allyl-5-(methylamino)-6-(3-nitrophenyl)-3-oxo-2,3-dihydropyridazine-4-carboxylate (J-1)

Intermediate J-1 was prepared following essentially the same procedure as described for Intermediate A by substituting methyl iodide with allyl bromide.

Ethyl 2-allyl-5-(2-chloro-N-methylacetamido)-6-(3-nitrophenyl)-3-oxo-2,3-dihydropyridazine-4-carboxylate (J-2)

A solution of 2-allyl-5-(methylamino)-6-(3-nitrophenyl)-3-oxo-2,3-dihydropyridazine-4-carboxylate (J-1) (1.20 g, 3.35 mmol) in chloroacetyl chloride (20 mL) was heated to reflux for 2 h. Then the excess of chloroacetyl chloride was removed in vacuo. The residue was purified by column chromatography on silica gel, eluting with PE/acetone (6:1-4:1) to give the title compound J-2 (0.63 g). MS-ESI (m/z): 435[M+1]$^+$.

6-Allyl-3-chloro-1-methyl-8-(3-nitrophenyl)pyrido [2,3-d]pyridazine-2,4,5(1H,3H,6H)-trione (Intermediate J)

To a solution of ethyl 2-allyl-5-(2-chloro-N-methylacetamido)-6-(3-nitrophenyl)-3-oxo-2,3-dihydropyridazine-4- carboxylate (J-2) (0.59 g, 1.36 mmol) in EtOH (20 mL) was added EtONa (92 mg, 1.36 mmol). The reaction mixture was diluted with EtOAc and water, 1 N HCl was added until pH=1-2. The organic phase was washed with water and brine, dried over MgSO$_4$ and concentrated. The residual was purified by column chromatography on silica gel, eluting with DCM/MeOH=100:1 to give the title compound Intermediate J (0.40 g). MS-ESI (m/z): 389 [M+1]$^+$.

Example 1

6-Cyclopropyl-3-fluoro-1-methyl-8-(3-nitrophenyl)-2,5-dioxo-1,2,5,6-tetrahydropyrido[2,3-d]pyridazin-4-yl trifluoromethanesulfonate (1a)

To a solution of 6-cyclopropyl-3-fluoro-4-hydroxy-1-methyl-8-(3-nitrophenyl)pyrido[2,3-d]pyridazine-2,5(1H,6H)-dione (Intermediate I) (1.44 g, 3.86 mmol) in anhydrous CH$_3$CN (55 mL) at 0° C. was added DIPEA (2.70 mL, 7.54 mmol) and 20 µL of NMP. After being stirred at 0° C. for 10 min, trifluoromethanesulfonic anhydride (1.06 g, 3.75 mmol) was added dropwise over 30 min. After being stirred at 0° C. to ambient temperature for 1 h, another portion of trifluoromethanesulfonic anhydride (1.06 g, 3.75 mmol) was added dropwise. The reaction system was purified by silica gel column, eluting with PE, DCM, 10% THF in DCM, to give the title compound 1a (1.84 g). MS-ESI (m/z): 505.0 [M+1]$^+$.

6-Cyclopropyl-3-fluoro-4-(2-fluoro-4-iodophenylamino)-1-methyl-8-(3-nitrophenyl)pyrido[2,3-d]pyridazine-2,5(1H,6H)-dione (1b)

A mixture of 6-cyclopropyl-3-fluoro-1-methyl-8-(3-nitrophenyl)-2,5-dioxo-1,2,5,6-tetrahydropyrido[2,3-d]pyridazin-4-yl trifluoromethanesulfonate (1a) (1.84 g, 3.64 mmol), 2-fluoro-4-iodoaniline (18.0 g, 75.6 mmol) and toluene (4 mL) was heated at 105° C. for 1.5 h. The residue was purified by chromatography on silica gel, eluting with PE, DCM, THF/DCM (1:100) to give product of 1b (720 mg). MS-ESI (m/z): 592.0 [M+1]$^+$.

8-(3-Aminophenyl)-6-cyclopropyl-3-fluoro-4-(2-fluoro-4-iodophenylamino)-1-methylpyrido[2,3-d]pyridazine-2,5(1H,6H)-dione (1c)

To a solution of 6-cyclopropyl-3-fluoro-4-(2-fluoro-4-iodophenylamino)-1-methyl-8-(3-nitrophenyl)pyrido[2,3-d]pyridazine-2,5(1H,6H)-dione 1b (720 mg, 1.22 mmol) in THF (20 mL) and ethanol (20 mL) was added stannous chloride hydrate (1.40 g, 6.08 mmol) at ambient temperature. The mixture was refluxed for 1.5 h. After cooling to ambient temperature, the mixture was quenched with 30% aqueous ammonia. The solid was removed by filtration. The filtrate was extracted with DCM. The extracts were washed with 30% aqueous ammonia, water, and brine, dried over Na$_2$SO$_4$ and concentrated to give the title compound 1c, which was used in next step without further purification. MS-ESI (m/z): 562.0 [M+1]$^+$.

N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide (1)

To a solution of 6-cyclopropyl-3-fluoro-4-(2-fluoro-4-iodophenylamino)-1-methyl-8-(3-nitrophenyl)pyrido[2,3-d]pyridazine-2,5(1H,6H)-dione 1c (47 mg, 0.084 mmol) and TEA (300 µL, 2.1 mmol) in DCM (1 mL) was added acetyl chloride (30 µL, 0.335 mmol) at 0° C. After being stirred at ambient temperature for 1.5 h, the mixture was diluted with DCM, washed with water and brine, dried over Na$_2$SO$_4$, and concentrated. The residue was purified by column chromatography on silica gel, eluting with DCM/MeOH (66:1) to give the title compound 1 (16 mg). MS-ESI (m/z): 604 [M+1]$^+$.

Example 2

N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide (2)

The title compound 2 was prepared following the same procedure as described for Example 1 by substituting acetyl chloride with propionyl chloride. MS-ESI (m/z): 618.0 [M+1]$^+$.

Example 3

N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide (3)

The title compound 3 was prepared following the same procedure as described for Example 1 by substituting acetyl chloride with isobutyryl chloride. MS-ESI (m/z): 632 [M+1]$^+$.

Example 4

N-(3-(6-cyclopropyl-3 fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide (4)

The title compound 4 was prepared following the same procedure as described for Example 1 by substituting acetyl chloride with cyclopropanecarbonyl chloride. MS-ESI (m/z):630 [M+1]$^+$.

Example 5

N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide (5)

To a solution of 6-cyclopropyl-3-fluoro-4-(2-fluoro-4-iodophenylamino)-1-methyl-8-(3-nitrophenyl)pyrido[2,3-d]pyridazine-2,5(1H,6H)-dione 1c (47 mg, 0.084 mmol) in pyridine (2 mL) was added methanesulfonyl chloride (19 µl, 0.25 mmol) at 0° C. After being stirred at 0° C.-room temperature for 3 h, the mixture was diluted with DCM. The solution was washed with 1 N HCl, water and brine, dried over Na$_2$SO$_4$ and concentrated. The residue was purified by column chromatography on silica gel to give title compound 5 (17.2 mg). MS-ESI (m/z): 640.0 [M+1]$^+$.

Example 6

N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide (6)

The title compound 6 was prepared following the same procedure as described for Example 5 by substituting methanesulfonyl chloride with ethanesulfonyl chloride. MS-ESI (m/z): 654.0 [M+1]$^+$.

Example 7

N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide (7)

The title compound 7 was prepared following the same procedure as described for Example 5 by substituting methanesulfonyl chloride with propane-2-sulfonyl chloride. MS-ESI (m/z): 668 [M+1]$^+$.

Example 8

N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide (8)

The title compound 8 was prepared following the same procedure as described for Example 5 by substituting methanesulfonyl chloride with cyclopropanesulfonyl chloride. MS-ESI (m/z): 666 [M+1]$^+$.

Following essentially the same procedures outlined for Examples 1-8, the compounds of Examples 9-34 listed in Table 2 were prepared from the corresponding intermediates listed in Table 1. The name and structure of Examples 9-34 are given below.

TABLE 2

| EXAMPLE | NAME | DATA |
|---|---|---|
| 9 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)acetamide | MS-ESI (m/z): 606 [M + 1]$^+$ |
| 10 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propionamide | MS-ESI (m/z): 620 [M + 1]$^+$ |
| 11 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)isobutyramide | MS-ESI (m/z): 634 [M + 1]$^+$ |
| 12 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanecarboxamide | MS-ESI (m/z): 632 [M + 1]$^+$ |
| 13 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)methanesulfonamide | MS-ESI (m/z): 642 [M + 1]$^+$ |
| 14 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)ethanesulfonamide | MS-ESI (m/z): 656 [M + 1]$^+$ |
| 15 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propane-2-sulfonamide | MS-ESI (m/z): 670 [M + 1]$^+$ |
| 16 | N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanesulfonamide | MS-ESI (m/z): 668 [M + 1]$^+$ |
| 17 | N-(3-(3-fluoro-4-(2-fluoro-4-iodophenylamino)-1-methyl-2,5-dioxo-6-propyl-1,2,5,6-tetrahydropyrido[2,3-d]pyridazin-8-yl)phenyl)cyclopropanesulfonamide | MS-ESI (m/z): 668.0 [M + H]$^+$ |
| 18 | N-(3-(3-fluoro-4-(2-fluoro-4-iodophenylamino)-6-(2-methoxyethyl)-1-methyl-2,5-dioxo-1,2,5,6-tetrahydropyrido[2,3-d]pyridazin-8-yl)phenyl)cyclopropanesulfonamide | MS-ESI (m/z): 684 [M + 1]$^+$ |
| 19 | N-(3-(3-fluoro-4-(2-fluoro-4-iodophenylamino)-6-(2-fluoroethyl)-1-methyl-2,5-dioxo-1,2,5,6-tetrahydropyrido[2,3-d]pyridazin-8-yl)phenyl)cyclopropanesulfonamide | MS-ESI (m/z): 672 [M + 1]$^+$ |
| 20 | N-(3-(6-(2,2-difluoroethyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide | MS-ESI (m/z): 690 [M + 1]$^+$ |
| 21 | N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)acetamide | MS-ESI (m/z): 578 [M + 1]$^+$ |
| 22 | N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)methanesulfonamide | MS-ESI (m/z): 614 [M + 1]$^+$ |
| 23 | N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)cyclopropanesulfonamide | MS-ESI (m/z): 640 [M + 1]$^+$ |
| 24 | N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide | MS-ESI (m/z): 592 [M + 1]$^+$ |

TABLE 2-continued

| EXAMPLE | NAME | DATA |
|---|---|---|
| 25 | N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide | MS-ESI (m/z): 628 [M + 1]$^+$ |
| 26 | N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide | MS-ESI (m/z): 656 [M + 1]$^+$ |
| 27 | N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide | MS-ESI (m/z): 654 [M + 1]$^+$ |
| 28 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide | MS-ESI (m/z): 604 [M + 1]$^+$ |
| 29 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide | MS-ESI (m/z): 618 [M + 1]$^+$ |
| 30 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide | MS-ESI (m/z): 630 [M + 1]$^+$ |
| 31 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide | MS-ESI (m/z): 640 [M + 1]$^+$ |
| 32 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide | MS-ESI (m/z): 654 [M + 1]$^+$ |
| 33 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide | MS-ESI (m/z): 668 [M + 1]$^+$ |
| 34 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide | MS-ESI (m/z): 666 [M + 1]$^+$ |
| 35 | N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide | MS-ESI (m/z): 632 [M + 1]$^+$ |

Example 36

N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)acetamide (36)

The title compound 36 was prepared following the same procedure as described for Example 1 by substituting Intermediate I with Intermediate D and 2-fluoro-4-iodoaniline with 4-bromo-2-fluoroaniline.

Example 37

N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)methanesulfonamide (37)

The title compound 37 was prepared following the same procedure as described for Example 1 and Example 5 by substituting intermediate I with intermediate D and 2-fluoro-4-iodoaniline with 4-bromo-2-fluoroaniline.

Example 38

N-(3-(6-allyl-3-chloro-4-(2-fluoro-4-iodophenylamino)-1-methyl-2,5-dioxo-1,2,5,6-tetrahydropyrido[2,3-d]pyridazin-8-yl)phenyl)acetamide (38)

6-Allyl-3-chloro-1-methyl-8-(3-nitrophenyl)-2,5-dioxo-1,2,5,6-tetrahydropyrido[2,3-d]pyridazin-4-yl 4-methylbenzenesulfonate (38a)

To a solution of 6-allyl-3-chloro-1-methyl-8-(3-nitrophenyl)pyrido[2,3-d]pyridazine-2,4,5(1H,3H,6H)-trione (Intermediate J, 0.100 g, 0.258 mmol) in DCM (5 mL) at ambient temperature was added TsCl (148 mg, 0.774 mmol), TEA (78 mg, 0.774 mmol) and catalytic amount of DMAP. After being stirred at ambient temperature for 1.5 h, the mixture was concentrated and purified by column chromatography on silica gel, eluting with PE: EtOAc=5:1 then to 2:1 to give the title compound 38a (20 mg). MS-ESI (m/z): 543 [M+1]$^+$.

6-allyl-3-chloro-4-((2-fluoro-4-iodophenyl)amino)-1-methyl-8-(3-nitrophenyl)pyrido[2,3-d]pyridazine-2,5(1H,6H)-dione (38b)

To a solution of 6-allyl-3-chloro-1-methyl-8-(3-nitrophenyl)-2,5-dioxo-1,2,5,6-tetrahydropyrido[2,3-d]pyridazin-4-yl 4-methylbenzenesulfonate 38a (20 mg, 0.037 mmol) and 2-fluoro-4-iodoaniline (8.77 mg, 0.0377 mmol) in THF (1 mL) at ambient temperature was added 60% NaH (20 mg). After being stirred at rt for 1 h, the reaction mixture was quenched with water and extracted with DCM. The extracts were washed with water and brine, dried over Na$_2$SO$_4$ and concentrated to give the title compound 38b (9 mg). MS-ESI (m/z): 608 [M+1]$^+$.

6-Allyl-8-(3-aminophenyl)-3-chloro-4-((2-fluoro-4-iodophenyl)amino)-1-methylpyrido[2,3-d]pyridazine-2,5(1H,6H)-dione (38c)

To a solution of 6-allyl-3-chloro-4-((2-fluoro-4-iodophenyl)amino)-1-methyl-8-(3-nitrophenyl)pyrido[2,3-d]

pyridazine-2,5(1H,6H)-dione 38b (9 mg, 0.0148 mmol) in THF/EtOH (6 mL, v/v=1:1) was added SnCl$_2$.2H$_2$O (17 mg). After being stirred at 70° C. for 2 h, the mixture was diluted with DCM/i-PrOH (v/v=4:1). The solution was washed with ammonium hydroxide, water and brine, dried over Na$_2$SO$_4$ and concentrated to give the title compound 38c, which was used directly in next step without further purification. MS-ESI (m/z): 577 [M+1]$^+$ N-(3-(6-allyl-3-chloro-4-((2-fluoro-4-iodophenyl) amino)-1-methyl-2,5-dioxo-1,2,5,6-tetrahydropyrido [2,3-d]pyridazin-8-yl)phenyl)acetamide (38)

To a solution of the crude product 38c from Step C in THF (0.5 mL) was added TEA (20 µL) and acetyl chloride (15 µL). The reaction mixture was stirred at ambient temperature for 1 h, diluted with water and extracted with DCM. The extract was washed with water and brine, dried over Na$_2$SO$_4$ and concentrated. The residue was purified by preparative TLC to give the title compound 38 (4.5 mg). MS-ESI (m/z): 620 [M+1]$^+$.

Example 39

N-(3-(3-chloro-6-(2,3-dihydroxypropyl)-4-((2-fluoro-4-iodophenyl)amino)-1-methyl-2,5-dioxo-1,2, 5,6-tetrahydropyrido[2,3-d]pyridazine-8-yl)phenyl) acetamide (39)

To a solution of N-(3-(6-allyl-3-chloro-4-((2-fluoro-4-iodophenyl)amino)-1-methyl-2,5-dioxo-1,2,5,6-tetrahydropyrido[2,3-d]pyridazin-8-yl)phenyl)acetamide 38 (2.7 mg) in THF/water (1 mL, v/v=1:1) was added NMO (cat.) followed by OsO$_4$ in toluene (20 mg/mL, 0.1 mL). After being stirred at rt for 12 h, the mixture was quenched with saturated aq. Na$_2$SO$_3$ and extracted with DCM. The extract was washed with water and brine, dried over Na$_2$SO$_4$ and concentrated to give the title compound 39 (2.6 mg). MS-ESI (m/z): 654 [M+1]$^+$.

Following essentially the same procedures outlined for Examples 39, the compounds of Examples 39-46 listed in Table 3 were prepared from the compounds of Examples 28-34 listed in Table 2 respectively. The names and structures of the compounds of Examples 40-46 are given below.

Example 47

N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylmethanesulfonamide (47)

To a solution of N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide (5) (100 mg, 0.156 mmol) and K$_2$CO$_3$ in DMF (10 mL) was added methyl iodide (22 mg, 0.156 mmol) dropwise at room temperature. After being stirred at room temperature for 1 h, the reaction mixture was extracted with EtOAc. The extracts were washed with water and brine, dried over Na$_2$SO$_4$ and concentrated to give the title compound 47 (54 mg) as yellow solid. MS-ESI (m/z): 654 [M+1]$^+$.

Example 48

N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylpropane-2-sulfonamide (48)

The title compound 48 was prepared following the same procedure as described for Example 47 by substituting compound 5 with compound 7. MS-ESI (m/z): 682 [M+1]$^+$.

Example 49

N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylcyclopropanesulfonamide (49)

The title compound 49 was prepared following the same procedure as described for Example 47 by substituting compound 5 with compound 8. MS-ESI (m/z): 680 [M+1]$^+$.

TABLE 3

| EXAMPLE | NAME | DATA |
| --- | --- | --- |
| 40 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)acetamide | MS-ESI (m/z): 638 [M + 1]$^+$ |
| 41 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propionamide | MS-ESI (m/z): 652 [M + 1]$^+$ |
| 42 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide | MS-ESI (m/z): 664 [M + 1]$^+$ |
| 43 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide | MS-ESI (m/z): 674 [M + 1]$^+$ |
| 44 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide | MS-ESI (m/z): 688 [M + 1]$^+$ |
| 45 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide | MS-ESI (m/z): 702 [M + 1]$^+$ |
| 46 | N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide | MS-ESI (m/z): 700 [M + 1]$^+$ |

Example 50

N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylmethanesulfonamide (50)

The title compound 50 was prepared following the same procedure as described for Example 47 by substituting compound 5 with compound 22. MS-ESI (m/z): 628 $[M+1]^+$.

Example 51

N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)propane-2-sulfonamide (51a)

Following essentially the same procedures outlined for Examples 7, the titled compound 51a were prepared from intermediates A. MS-ESI (m/z): 642 $[M+1]^+$.

N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylpropane-2-sulfonamide (51)

The title compound 51 was prepared following the same procedure as described for Example 47 by substituting compound 5 with compound 51a. MS-ESI (m/z): 656 $[M+1]^+$.

Example 52

N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylcyclopropanesulfonamide (52)

The title compound 52 was prepared following the same procedure as described for Example 47 by substituting compound 5 with compound 23. MS-ESI (m/z): 654 $[M+1]^+$.

Example 53

6-cyclopropyl-3-fluoro-4-((2-fluoro-4-iodophenyl)amino)-1-methyl-8-(3-(2-oxopyrrolidin-1-yl)phenyl)pyrido[2,3-d]pyridazine-2,5(1H,6H)-dione (53)

To a solution of 8-(3-Aminophenyl)-6-cyclopropyl-3-fluoro-4-(2-fluoro-4-iodophenylamino)-1-methylpyrido[2,3-d]pyridazine-2,5(1H,6H)-dione (1c) (84 mg, 0.15 mmol) and triethylamine (64 mg, 0.60 mmol) in dichloromethane (10 mL) was added 4-chlorobutanoyl chloride (63 mg, 0.45 mmol) dropwise at room temperature. After being stirred at room temperature for 1 h, the reaction mixture was extracted with DCM. The extracts were washed with water and brine, dried over $Na_2SO_4$ and concentrated. The residue was dissolved in DMF (5 mL) followed by addition of DBU (45.6 mg, 0.30 mmol). The reaction mixture was stirred at room temperature for 1 h and was extracted with EtOAc. The extracts were washed with water and brine, dried over $Na_2SO_4$ and concentrated to give the title compound 53 (45 mg) as yellow solid. MS-ESI (m/z): 630 $[M+1]^+$.

Example 54

8-(3-aminophenyl)-3-fluoro-4-(2-fluoro-4-iodophenylamino)-1,6-dimethylpyrido[2,3-d]pyridazine-2,5(1H,6H)-dione (54a)

The title compound 54a was prepared following the same procedure as described for Compound 1c by substituting Intermediate I with Intermediate A. MS-ESI (m/z): 535 $[M+1]^+$.

3-fluoro-4-((2-fluoro-4-iodophenyl)amino)-1,6-dimethyl-8-(3-(2-oxopyrrolidin-1-yl)phenyl)pyrido[2,3-d]pyridazine-2,5(1H,6H)-dione (54)

The title compound 54 was prepared following the same procedure as described for Example 53 by substituting compound 1c with compound 54a. MS-ESI (m/z): 604 $[M+1]^+$.

Example 55

6-cyclopropyl-8-(3-(1,1-dioxidoisothiazolidin-2-yl)phenyl)-3-fluoro-4-((2-fluoro-4-iodophenyl)amino)-1-methylpyrido[2,3-d]pyridazine-2,5(1H,6H)-dione (55)

To a solution of 8-(3-Aminophenyl)-6-cyclopropyl-3-fluoro-4-(2-fluoro-4-iodophenylamino)-1-methylpyrido[2,3-d]pyridazine-2,5(1H,6H)-dione (1c) (84 mg, 0.15 mmol) in pyridine (2 mL) was added 3-chloropropane-1-sulfonyl chloride (80 mg, 0.45 mmol) dropwise at room temperature. After being stirred at room temperature for 1 h, the reaction mixture was extracted with DCM. The extracts were washed with water and brine, dried over $Na_2SO_4$ and concentrated. The residue was dissolved in DMF (5 mL) followed by addition of DBU (45.6 mg, 0.30 mmol). The reaction mixture was stirred at room temperature for 1 h and was extracted with EtOAc. The extracts were washed with water and brine, dried over $Na_2SO_4$ and concentrated to give the title compound 55 (55 mg) as yellow solid. MS-ESI (m/z): 666 $[M+1]^+$.

Example 56

8-(3-(1,1-dioxidoisothiazolidin-2-yl)phenyl)-3-fluoro-4-((2-fluoro-4-iodophenyl)amino)-1,6-dimethylpyrido[2,3-d]pyridazine-2,5(1H,6H)-dione (56)

The title compound 56 was prepared following the same procedure as described for Example 55 by substituting compound 1c with compound 54a. MS-ESI (m/z): 640 $[M+1]^+$.

Reference Compound 4-((2-fluoro-4-methylphenyl)amino)-1,3,8-trimethylpyrido[2,3-d]pyridazine-2,5(1H,6H)-dione (57)(Example 165 of U.S. Pat. No. 7,517,994)

Ethyl 4,4-dicyano-2-methyl-3-oxobutanoate (57a)

To a solution of malononitrile (76 g, 1.18 mol) and diethyl methylmalonate (200 g, 1.15 mol) in THF (1200 ml) was added DBU (350 g, 2.3 mol) at −50° C., and the mixture was warmed to RT and stirred overnight. The mixture was diluted with EA (4000 ml), washed with 2 N HCl (2000 ml)

and brine (2000 ml), dried over Na$_2$SO$_4$, and concentrated to dryness. The residue was purified by column chromatography to give the title compound 57a (15 g).

2-amino-4-hydroxy-1,5-dimethyl-6-oxo-1,6-dihydropyridine-3-carbonitrile (57b)

A mixture of ethyl 4,4-dicyano-2-methyl-3-oxobutanoate (57a) (9 g, 46.4 mmol) and methylamine (30% methanol solution, 150 ml, 1.45 mol) was stirred at RT for 40 h. The reaction mixture was concentrated in vacuo and diluted with methanol (150 ml). The solution was added sodium methanolate (7.5 g, 139 mmol) and stirred at 55° C. for 2 h, then cooled to 0~5° C. The pH of the mixture was adjusted to 2~3 by addition of HCl (12 N). The resulting mixture was concentrated in vacuo, the residue was diluted with THF and filtrated, the filtrate was concentrated and purified by column chromatography to give the title compound 57b (2.2 g). MS-ESI (m/z): 180 [M+1]$^+$.

2-Amino-4-chloro-1,5-dimethyl-6-oxo-1,6-dihydropyridine-3-carbonitrile (57c)

To a solution of 2-amino-4-hydroxy-1,5-dimethyl-6-oxo-1,6-dihydropyridine-3-carbonitrile (57b) (2.1 g, 11.7 mmol) in MeCN (40 ml) was added oxalyl dichloride (10.5 ml, 122.4 mmol) dropwise at 5° C., and the mixture was stirred at RT for 1 h. The reaction mixture was concentrated in vacuo to give the title compound 57c (2.6 g). MS-ESI (m/z): 198 [M+1]$^+$.

2-bromo-4-chloro-1,5-dimethyl-6-oxo-1,6-dihydropyridine-3-carbonitrile (57d)

To a suspension of CuBr (1.6 g, 11.2 mmol) and 2-amino-4-chloro-1,5-dimethyl-6-oxo-1,6-dihydropyridine-3-carbonitrile (57c) (2.6 g, 11.7 mmol) in MeCN (80 ml) was added t-butyl nitrite (2 g, 19.4 mmol), and the mixture was stirred at RT for 3 h. The reaction mixture was concentrated and purified by column chromatography to give the title compound 57d (1.6 g).

4-chloro-2-(1-ethoxyvinyl)-1,5-dimethyl-6-oxo-1,6-dihydropyridine-3-carbonitrile (57e)

A mixture of 2-bromo-4-chloro-1,5-dimethyl-6-oxo-1,6-dihydropyridine-3-carbonitrile (57d) (200 mg, 0.76 mmol), tributyl(1-ethoxyvinyl)stannane (820 mg, 2.27 mmol) and bis(triphenylphosphine)palladium(II) chloride (120 mg, 0.17 mmol) in THF (20 ml) was stirred under nitrogen at 70° C. for 14 h. The reaction mixture was quenched with aqueous KF solution (10%, 10 ml) and extracted with EA (20 ml). The organic layer was washed with brine, dried over Na$_2$SO$_4$, and purified by preparative thin layer chromatography to give the title compound 57e (70 mg). MS-ESI (m/z): 253 [M+1]$^+$.

2-acetyl-4-chloro-1,5-dimethyl-6-oxo-1,6-dihydropyridine-3-carbonitrile (57f)

To a solution of 4-chloro-2-(1-ethoxyvinyl)-1,5-dimethyl-6-oxo-1,6-dihydropyridine-3-carbonitrile (57e) (70 mg, 0.28 mmol) in MeCN (6 ml) was added hydrochloric acid (36%, 3 ml, 36 mmol), and the mixture was stirred at RT for 5 h. The reaction mixture was quenched with brine and extracted with EA, the organic layer was dried over Na$_2$SO$_4$ and purified by preparative thin layer chromatography to give the title compound 57f (24 mg). MS-ESI (m/z): 225 [M+1]$^+$.

4-chloro-1,3,8-trimethylpyrido[2,3-d]pyridazine-2,5 (1H,6H)-dione (57g)

To a solution of 2-acetyl-4-chloro-1,5-dimethyl-6-oxo-1,6-dihydropyridine-3-carbonitrile (57f) (2 mg, 8.9 μmol) and acetic acid (8 mg, 133 μmol) in 1,4-dioxane (0.5 ml) was added hydrazine hydrate (8 mg, 160 μmol), and the mixture was stirred at 70° C. for 44 h. The reaction mixture was concentrated in vacuo, the residue was diluted with EA, washed with water and brine, dried over Na$_2$SO$_4$ and purified by preparative thin layer chromatography to give the title compound 57f (0.8 mg). MS-ESI (m/z): 240 [M+1]$^+$.

4-((2-fluoro-4-methylphenyl)amino)-1,3,8-trimethylpyrido[2,3-d]pyridazine-2,5(1H,6H)-dione (57)

To a solution of 2-fluoro-4-methylaniline (1.3 mg, 10.4 μmol) and 4-chloro-1,3,8-trimethylpyrido[2,3-d]pyridazine-2,5(1H,6H)-dione (57g) (2.3 mg, 9.6 μmol) in THF (0.5 ml) was added lithium bis(trimethylsilyl)amide (1 M, 0.7 ml, 0.7 mmol) dropwise at −70° C., and the mixture was warmed to RT naturally, quenched with saturated aqueous ammonium chloride solution and extracted with EA. The EA layer was dried over Na$_2$SO$_4$ and purified by preparative thin layer chromatography to give the title compound 57 (1.5 mg). MS-ESI (m/z): 329 [M+1]$^+$.

Biological Activity

Materials and Preparation of Reagents

MTS testing kit was purchased from Promega. The DMEM, RPMI-1640 and Fetal bovine serum were purchased from Gibco. Dimethyl sulfoxide (DMSO) was purchased from Sigma.

Inhibition Activity of Cell Proliferation

To investigate whether a compound is able to inhibit the activity of MEK in cells, a mechanism-based assay using A-375 and HT-29 cell was developed. In this assay, inhibition of MEK was detected by the inhibition of A-375 and HT-29 cells proliferation. A-375 and HT-29 cells were cultured in culture flasks to 40-80% confluence respectively in DMEM and RPMI-1640 plus 10% fetal bovine serum. Cells were collected and plated onto 96-well plates at desired cell density (A-375: 3000 cells/well; HT-29: 5000 cells/well). Plates were incubated overnight at 37° C., with 5% CO$_2$ to adhere. Compounds were added to the plates. The final compound concentrations were 1000, 333.3, 111.1, 27.04, 12.35, 4.12, 1.37, 0.46 and 0.15 nM, respectively. Place plates at 37° C., with 5% CO$_2$ for 72 h. 10 μl MTS were added to each well and incubate the plates for exactly 2 hours. Absorbance was measured at 490 nm. IC$_{50}$ was calculated using GraphPad Prism 5.0.

Biological Data for Select Compounds

Select compounds prepared as described above were assayed according to the biological procedures described herein. The results are given in Table 4:

TABLE 4

| Example | A375 IC$_{50}$ (nM) | HT29 IC$_{50}$ (nM) |
|---|---|---|
| 1 | 1.2 | 2.4 |
| 2 | 10.6 | 13.7 |

TABLE 4-continued

| Example | A375 IC$_{50}$ (nM) | HT29 IC$_{50}$ (nM) |
|---|---|---|
| 3 | 15.3 | 41.4 |
| 4 | 26.6 | 41.9 |
| 5 | 4.0 | 5.1 |
| 6 | 4.8 | 6.4 |
| 7 | 3.5 | 4.1 |
| 8 | 5.4 | 5.4 |
| 9 | 44.0 | 47.3 |
| 10 | 61.2 | 59.6 |
| 11 | 198.3 | 180.3 |
| 12 | 199.0 | 192.4 |
| 13 | 26.2 | 87.4 |
| 14 | 19.6 | 6.4 |
| 15 | 34.9 | 151.7 |
| 16 | 19.4 | 31.5 |
| 17 | 12.8 | 21.6 |
| 18 | 30.2 | 23.6 |
| 19 | 2.4 | 4.2 |
| 20 | 6.4 | 7.7 |
| 21 | 3.9 | <1.0 |
| 22 | <1.0 | <1.0 |
| 23 | <1.0 | <1.0 |
| 24 | 13.7 | 6.1 |
| 25 | <1.0 | <1.0 |
| 26 | 11.9 | <1.0 |
| 27 | <1.0 | <1.0 |
| 28 | 1.6 | 6.4 |
| 29 | 51.2 | 105.5 |
| 30 | 80.7 | 76.7 |
| 31 | 1.1 | 7.4 |
| 32 | 36.2 | 12.7 |
| 33 | 12.6 | 7.2 |
| 34 | 4.2 | 4.6 |
| 35 | 26.3 | 22.6 |
| 36 | 341.2 | 426.8 |
| 37 | 32.4 | 42.7 |
| 38 | 20.8 | — |
| 39 | 22.8 | — |
| 40 | 2.5 | 1.9 |
| 41 | 398.7 | 314.6 |
| 42 | 179.9 | 112.5 |
| 43 | 3.6 | 4.6 |
| 44 | 71.3 | 57.7 |
| 45 | 9.8 | 23.5 |
| 46 | 68.9 | 24.2 |
| 47 | 4.9 | 16.6 |
| 48 | 3.4 | 13.2 |
| 49 | 2.5 | 11.7 |
| 50 | 1.5 | 5.3 |
| 51 | 2.2 | 2.0 |
| 52 | 5.7 | 7.8 |
| 53 | 7.8 | 19.1 |
| 54 | 4.7 | 7.9 |
| 55 | 8.8 | 18.7 |
| 56 | 9.3 | 14.1 |
| Reference Compound | >1000 | >1000 |

What is claimed is:

1. A compound of formula (I):

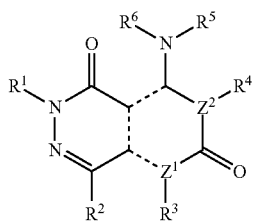

(I)

and/or a pharmaceutically acceptable salt thereof, wherein:

$Z^1$ is N;

$Z^2$ is C;

a

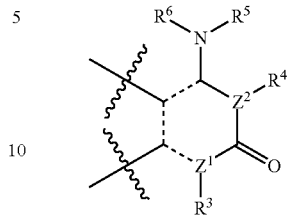

moiety is

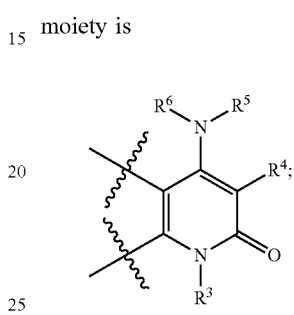

$R^1$ is selected from $C_{1-6}$ alkyl, $C_{2-6}$ alkenyl and $C_{3-10}$ cycloalkyl, wherein alkyl, alkenyl, and cycloalkyl are each unsubstituted or substituted with one, two, three, or four substituents independently selected from halogen and $OR^a$;

$R^2$ and $R^5$ are independently $(CH_2)_m$-Q, wherein

Q is aryl unsubstituted or substituted with one, two, three, or four substituents independently selected from $R^8$;

$R^3$ is $C_{1-6}$ alkyl;

$R^4$ is halogen;

$R^6$ is hydrogen;

each $R^8$ is independently selected from:

halogen, $N(R^a)C(=O)R^b$, and $N(R^a)S(=O)_2R^b$;

each $R^a$ is independently selected from hydrogen and $C_{1-6}$alkyl;

each $R^b$ is independently selected from:

$C_{1-6}$ alkyl and $C_{3-8}$ cycloalkyl;

or $R^a$ and $R^b$ together with the carbon atoms and/or heteroatoms to which they are attached can form a 4-10 membered ring containing 0, 1, 2 or 3 heteroatoms independently selected from sulfur and nitrogen; and m is 0.

2. A compound of claim 1, and/or a pharmaceutically acceptable salt thereof, wherein $R^1$ is methyl, ethyl, propyl, isopropyl, allyl, or cyclopropyl, each independently unsubstituted or substituted with one, two, three, or four substituents independently selected from halogen and $OR^a$, wherein $R^a$ is independently selected from hydrogen and $C_{1-6}$ alkyl.

3. A compound of claim 2, and/or a pharmaceutically acceptable salt thereof, wherein $R^a$ is independently selected from hydrogen and methyl.

4. A compound of claim 3, and/or a pharmaceutically acceptable salt thereof, wherein $R^1$ is methyl, ethyl, propyl, isopropyl, allyl, cyclopropyl, 2-fluoroethyl, 2,2-difluoroethyl, 2,3-dihydroxypropyl, or 2-methoxyethyl.

5. A compound of claim 1, and/or a pharmaceutically acceptable salt thereof, wherein $R^2$ is $(CH_2)_m$-Q, wherein m is 0, and Q is phenyl, which is unsubstituted or substituted with one, two, three, or four substituents independently selected from $R^8$, wherein $R^8$ is independently selected from $N(R^a)C(=O)R^b$ and $N(R^a)S(=O)_2R^b$.

6. A compound of claim 5, and/or a pharmaceutically acceptable salt thereof, wherein $R^a$ is hydrogen or methyl, and $R^b$ is independently selected from methyl, ethyl, isopropyl and cyclopropyl.

7. A compound of claim 5, and/or a pharmaceutically acceptable salt thereof, wherein $R^a$ and $R^b$ together with the carbon atoms and/or heteroatoms to which they are attached form a 5-6 membered ring containing 0, 1, 2 or 3 heteroatoms independently selected from sulfur and nitrogen.

8. A compound of claim 5, and/or a pharmaceutically acceptable salt thereof, wherein $R^8$ is independently selected from 2-oxopyrrolidin-1-yl and 1,1-dioxidoisothiazolidin-2-yl.

9. A compound of claim 1, and/or a pharmaceutically acceptable salt thereof, wherein $R^3$ is methyl.

10. A compound of claim 1, and/or a pharmaceutically acceptable salt thereof, wherein $R^4$ is fluorine or chlorine.

11. A compound of claim 1, and/or a pharmaceutically acceptable salt thereof, wherein $R^5$ is $(CH_2)_m$-Q, wherein m is 0 and Q is phenyl which is unsubstituted or substituted with one, two, three, or four substituents independently selected from halogen.

12. A compound of claim 11, and/or a pharmaceutically acceptable salt thereof, wherein $R^5$ is 2-fluoro-4-iodophenyl or 4-bromo-2-fluorophenyl.

13. A compound of claim 1, selected from:
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide,
N-(3-(6-cyclopropyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)acetamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propionamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)isobutyramide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanecarboxamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)methanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)ethanesulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)propane-2-sulfonamide,
N-(3-(3-fluoro-4-(2-fluoro-4-iodophenylamino)-6-isopropyl-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-1-methyl-2,5-dioxo-6-propyl-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-(2-methoxyethyl)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-6-(2-fluoroethyl)-1-methyl-2,5-dioxo-1,2,5,6-tetrahydropyrido[2,3-d]pyridazin-8-yl)phenyl)cyclopropanesulfonamide,
N-(3-(6-(2,2-difluoroethyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)acetamide,
N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)methanesulfonamide,
N-(3-(3-fluoro-4-(2-fluoro-4-iodophenylamino)-1,6-dimethyl-2,5-dioxo-1,2,5,6-tetrahydropyrido[2,3-d]pyridazin-8-yl)phenyl)cyclopropanesulfonamide,
N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide,
N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-ethyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propionamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide, N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide,
N-(3-(6-allyl-3-fluoro-4-(2-fluoro-4-iodophenylamino)-1-methyl-2,5-dioxo-1,2,5,6-tetrahydropyrido[2,3-d]pyridazin-8-yl)phenyl)isobutyramide,
N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)acetamide,
N-(3-(6-allyl-4-(4-bromo-2-fluorophenylamino)-3-fluoro-1-methyl-2,5-dioxo-1,2,5,6-tetrahydropyrido[2,3-d]pyridazin-8-yl)phenyl)methanesulfonamide,
N-(3-(6-allyl-3-chloro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(3-chloro-6-(2,3-dihydroxypropyl)-4-((2-fluoro-4-iodophenyl)amino)-1-methyl-2,5-dioxo-1,2,5,6-tetrahydropyrido[2,3-d]pyridazin-8-yl)phenyl)acetamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)acetamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propionamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanecarboxamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)methanesulfonamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)ethanesulfonamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-(2,3-dihydroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide,
N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylmethanesulfonamide,
N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylpropane-2-sulfonamide,
N-(3-(6-cyclopropyl-3-fluoro-4-((2-fluoro-4-iodophenyl)amino)-1-methyl-2,5-dioxo-1,2,5,6-tetrahydropyrido[2,3-d]pyridazin-8-yl)phenyl)-N-methylcyclopropanesulfonamide,
N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylmethanesulfonamide,
N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylpropane-2-sulfonamide,
N-(3-(3-fluoro-4-((2-fluoro-4-iodophenyl)amino)-1,6-dimethyl-2,5-dioxo-1,2,5,6-tetrahydropyrido[2,3-d]pyridazin-8-yl)phenyl)-N-methylcyclopropanesulfonamide,
6-cyclopropyl-3-fluoro-4-((2-fluoro-4-iodophenyl)amino)-1-methyl-8-(3-(2-oxopyrrolidin-1-yl)phenyl)pyrido[2,3-d]pyridazine-2,5(1H,6H)-dione,
3-fluoro-4-((2-fluoro-4-iodophenyl)amino)-1,6-dimethyl-8-(3-(2-oxopyrrolidin-1-yl)phenyl)pyrido[2,3-d]pyridazine-2,5(1H,6H)-dione,
6-cyclopropyl-8-(3-(1,1-dioxidoisothiazolidin-2-yl)phenyl)-3-fluoro-4-((2-fluoro-4-iodophenyl)amino)-1-methylpyrido[2,3-d]pyridazine-2,5(1H,6H)-dione, and
8-(3-(1,1-dioxidoisothiazolidin-2-yl)phenyl)-3-fluoro-4-((2-fluoro-4-iodophenyl)amino)-1,6-dimethylpyrido[2,3-d]pyridazine-2,5(1H,6H)-dione.

14. A pharmaceutical composition, comprising a compound of claim 1, and/or a pharmaceutically acceptable salt thereof, and at least one pharmaceutically acceptable carrier.

15. A method for modulating MEK, comprising administering to a subject in need thereof a therapeutically effective amount of a compound of claim 1, and/or a pharmaceutically acceptable salt thereof, or a pharmaceutical composition thereof.

\* \* \* \* \*

UNITED STATES PATENT AND TRADEMARK OFFICE
CERTIFICATE OF CORRECTION

PATENT NO. : 9,556,171 B2
APPLICATION NO. : 14/785205
DATED : January 31, 2017
INVENTOR(S) : Wang et al.

Page 1 of 2

It is certified that error appears in the above-identified patent and that said Letters Patent is hereby corrected as shown below:

In the Specification

On Column 18, Line 5:
Replace "6-allyl"
With --6-cyclopropyl--.

On Column 18, Line 24:
Replace "6-allyl"
With --6-cyclopropyl--.

On Column 20, Lines 14-15:
Replace "propane-2-sulfonamide"
With --cyclopropanesulfonamide--.

On Column 34, Line 46:
Replace "Intermediate A"
With --Intermediate A-8--.

On Column 35, Lines 65-67:
Replace "6-cyclopropyl-3-fluoro-4-(2-fluoro-4-iodophenylamino)-1-methyl-8-(3-nitrophenyl)pyrido[2,3-d]pyridazine-2,5(1H,6H)-dione (1c)"
With --8-(3-Aminophenyl)-6-cyclopropyl-3-fluoro-4-(2-fluoro-4-iodophenylamino)-1-methylpyrido[2,3-d]pyridazine-2,5-(1H,6H)-dione (1c)--.

On Column 36, Line 13:
Replace "6-allyl"
With --6-cyclopropyl--.

Signed and Sealed this
Ninth Day of October, 2018

Andrei Iancu
*Director of the United States Patent and Trademark Office*

CERTIFICATE OF CORRECTION (continued)
U.S. Pat. No. 9,556,171 B2

On Column 36, Lines 58-60:
Replace "6-cyclopropyl-3-fluoro-4-(2-fluoro-4-iodophenylamino)-1-methyl-8-(3-nitrophenyl)pyrido[2,3-d]pyridazine-2,5(1H,6H)-dione (1c)"
With --8-(3-Aminophenyl)-6-cyclopropyl-3-fluoro-4-(2-fluoro-4-iodophenylamino)-1-methylpyrido[2,3-d]pyridazine-2,5-(1H,6H)-dione (1c)--.

On Column 38, Line 7:
Replace "6-allyl"
With --6-cyclopropyl--.

On Column 38, Line 18:
Replace "Examples 9-34"
With --Examples 9-35--.

On Column 38, Line 20:
Replace "Examples 9-34"
With --Examples 9-35--.

On Column 40, Line 45:
Replace "(1H,6H]"
With --(1H,6H)--.

On Column 41, Line 41:
Replace "Examples 39-46"
With --Examples 40-46--.

On Columns 41-42, last entry for Table 3:
Replace "N-(3-(6-(2,3-dihyroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)propane-2-sulfonamide"
With --N-(3-(6-(2,3-dihyroxypropyl)-3-fluoro-4-(2-fluoro-4-iodophenylamino)-1-methyl-2,5-dioxo-1,2,5,6-tetrahydropyrido[2,3-d]pyridazin-8-yl)phenyl)cyclopropanesulfonamide--.

In the Claims

In Claim 13, Line 40 of Column 49:
Replace "6-allyl"
With --6-cyclopropyl--.

In Claim 13, Line 62 of Column 49:
Replace "6-allyl"
With --6-cyclopropyl--.

In Claim 13, Lines 3-4 of Column 52:
Replace "propane-2-sul-fonamide"
With --cyclopropanesulfonamide--.